US007615543B2

(12) United States Patent
Pepys

(10) Patent No.: US 7,615,543 B2
(45) Date of Patent: Nov. 10, 2009

(54) TREATMENT AND PREVENTION OF TISSUE DAMAGE

(75) Inventor: Mark B Pepys, London (GB)

(73) Assignee: Pentraxin Therapeutics Limited, London (GB)

( * ) Notice: Subject to any disclaimer, the term of this patent is extended or adjusted under 35 U.S.C. 154(b) by 287 days.

(21) Appl. No.: 10/514,127

(22) PCT Filed: May 14, 2003

(86) PCT No.: PCT/GB03/02096

§ 371 (c)(1),
(2), (4) Date: Jul. 6, 2005

(87) PCT Pub. No.: WO03/097104

PCT Pub. Date: Nov. 27, 2003

(65) Prior Publication Data

US 2006/0019930 A1    Jan. 26, 2006

(30) Foreign Application Priority Data

May 15, 2002  (GB)  ................................. 0211136.7

(51) Int. Cl.
*A61K 31/66* (2006.01)
(52) U.S. Cl. ..................... 514/75; 424/179.1
(58) Field of Classification Search .................. None
See application file for complete search history.

(56) References Cited

U.S. PATENT DOCUMENTS

| 4,640,913 | A | 2/1987 | Wissner et al. |
| 5,064,817 | A | 11/1991 | Yedgar et al. |
| 5,681,829 | A | 10/1997 | Tempesta et al. |
| 5,811,568 | A | 9/1998 | Bierer et al. |
| 6,764,826 | B2 | 7/2004 | Yeh et al. |
| 2003/0171251 | A1* | 9/2003 | Pepys ............................ 514/1 |

FOREIGN PATENT DOCUMENTS

| JP | 2001-302485 | 10/2001 |
| JP | 2001 302485 | * 10/2001 |
| WO | WO 01/94951 | 12/2001 |
| WO | WO 03/013508 A1 | 2/2003 |

OTHER PUBLICATIONS

Bourla et al., "Age-related macular degeneration: a practical approach to a challenging disease", J Am Geriatr Soc 54: 1130-1135 (2006).*
Lu et al., "Synthetic Analogues of Irlbacholine: A Novel Antifungal Plant Metabolite Isolated form Irlbachia Alata", J. Nat. Prod. 62: 824-828 (1999).*
Pepys et al., Targeted pharamacological depletion of serum amyloid P component for treatment of human anyloidosis, Nature, 2002 Macmillan Magazines Ltd., pp. 254-259, (May 16, 2002).

Christner et al., Binding of Human Serum Amyloid P-Component to Phosphocholine, Archives of Biochemistry and Biophysics, Academic Press, Inc., vol. 314 ( No. 2), pp. 337-343, (Nov. 1, 1994).
Liuzzo et al., The Prognostic Value of C-Reactive Protein and Serum Amyloid A Protein in Severe Unstable Angina, The New England Journal of Medicine, 1st ed., Massachusetts Medical Society, vol. 331 ( No. 7), pp. 417-424, 1994.
Hirschfield et al., Therapeutic inhibition of C-reactive protein—novel drugs, novel mechanisms, Medical Research Society, abstract, Feb. 5, 2003.
Baltz, M.L., de Beer, F.C., Feinstein, A., Munn, E.A., Milstein, C.P., Fletcher, T.C., March, J.F., Taylor, J., Bruton, C., Clamp, J.R., Davies, A.J.S. and Pepys, M.B. (1982) Phylogenetic aspects of C-reactive protein and related proteins: *Ann. N. Y. Acad Sci.*, 389: 49-75.
Beranek, J.T. (1997) C-reactive protein and complement in myocardial infarction and postinfarction heart failure. *Eur. Heart J.*, 18: 1834-1835.
Beranek, J.T. (1998) C-reactive protein in postinfarction heart rupture. *Am. Heart J.*, 136: 563-564.
Berman et al., (1986) Binding of C-Reactive Protein to Nucleated Cells Leads to Complement Activation without Cytolysis, *J. Immunol.*, 136(4): 1354-1359.
Bhakdi et al., Possible Protective Role for C-Reactive Protein in Atherogenesis, *Circulation*, p. 1870-1876 (2001a).
Bhakdi et al., Beyond Cholesterol: the Enigma of Artherosclerosis Revisited, *Thromb. Haemost.*, p. 639-645 (2004b).
Bhakdi, S., Dorweiler, B., Kirchmann, R., Torzewski, J., Weise, E., Tranum-Jensen, J., Walev, I. and Wieland, E. (1995) On the pathogenesis of atherosclerosis: enzymatic transformation of human low density lipoprotein to an atherogenic moiety. *J. Exp. Med*, 182: 1959-1971.
Bhakdi, S., Torzewski, M., Klouche, M. and Hemmes, M. (1999) Complement and atherogenesis. Binding of CRP to degraded, nonoxidized LDL enhances complement activation. *Arterioscler. Thromb. Vasc. Biol.*, 19: 2348-2354.
Bickerstaff, M.C.M., Botto, M., Hutchinson, W.L., Herbert, J., Tennent, G.A., Bybee, A., Mitchell, D.A., Cook, H.T., Butler, P.J.G., Walport, M.J. and Pepys, M.B. (1999) Serum amyloid P component controls chromatin degradation and prevents antinuclear autoimmunity. *Nature Med.*, 5: 694-697.
Boralessa, H., de Beer, F.C., Manchie, A. Whitwam, J.G. and Pepys, M.B. (1986) C-reactive protein in patients undergoing cardiac surgery. *Anaesthesia*, 41: 11-15.

(Continued)

*Primary Examiner*—Anand U Desai
(74) *Attorney, Agent, or Firm*—Frommer Lawrence & Haug LLP; Thomas J. Kowalski; Deborah L. Lu

(57) ABSTRACT

An agent for use in medicine, which agent comprises a plurality of ligands covalently co-linked so as to form a complex with a plurality of C-reactive protein (CRP) molecules in the presence thereof, wherein (i) at least two of the ligands are the same or different and are capable of being bound by ligand binding sites present on the CRP molecules; or (ii) at least one of the ligands is capable of being bound by a ligand binding site present on a CRP molecule, and at least one other of the ligands is capable of being bound by a ligand binding site present on a serum amyloid P component (SAP) molecule.

6 Claims, 10 Drawing Sheets

OTHER PUBLICATIONS

Cermak, J., Key, N.S., Bach, R.R., Balla, J., Jacob, H.S. and Vercellotti, G.M. (1993) C-reactive protein induces human peripheral blood monocytes to synthesize tissue factor. *Blood*, 82: 513-520.

Chang et al., (2002) C-Reactive Protein Binds to both Oxidized LDL and Apoptotic Cells Through Recognition of a Common Ligand: Phosphorylcholine of Oxidized Phospholipids, *Proc. Natl. Acad. Sci. U.S.A.*, vol. 99 (No. 20) p. 13043-13048.

Claus, D.R., Siegel, J., Petras, K., Osmand, A.P. and Gewurz, H. (1977) Interactions of C-reactive protein with the first component of human complement. *J. Immunol.*, 119: 187-192.

Culley, F.J., Bodman-Smith, K.B., Ferguson, M.A.J., Nikolaev, AN., Shantilal, N. and Raynes, J.G. (2000) C-reactive protein binds to phosphorylated carbohydrates. *Glycobiology*, 10: 59-65.

Danesh, J., Collins, R., Appleby, P. and Peto, R. (1998) Association of fibrinogen, C-reactive protein, albumin, or leukocyte count with coronary heart disease. *J. Am. Coll. Cardiol.*, 279: 1477-1482.

Danesh, J., Whincup, P., Walker, M., Lennon, L., Thomson, A., Appleby, P., Gallimore, J.R. and Pepys, M.B. (2000) Low-grade inflammation and coronary heart disease: new prospective studies and updated meta-analyses. *B.MJ*, 321: 199-204.

de Beaufort, A.J., Langermans, J.A.M., Matze-van der Lans, A.M., Hiemstra, P.S., Vossen, J.M. and Van Furth, R. (1997) Difference in binding of killed and live *Streptococcus pneumoniae* serotypes by C-reactive protein. *Scand. J. Immunol.*, 46: 597-600.

de Beer, F.C., Baltz, M.L., Munn, E.A., Feinstein, A., Taylor, J., Bruton, C., Clamp, J.R. and Pepys, M.B. (1982) Isolation and characterisation of C-reactive protein and serum amyloid P component in the rat. *Immunology*, 45: 55-70.

de Beer, F.C., Hind, C.R.K., Fox, K.M., Allan, R., Maseri, A. and Pepys, M.B. (1982) Measurement of serum C-reactive protein concentration in myocardial ischaemia and infarction. *Br. Heart J*, 47: 239-243.

de Beer, F.C., Soutar, A.K., Baltz, M.L., Trayner, I., Feinstein, A. and Pepys, M.B. (1982) Low density and very low density lipoproteins are selectively bound by aggregated C-reactive protein. J. *Exp. Med*, 156: 230-242.

de Winter, R.J., Bholasingh, R., Lijmer, J.G., Koster, R.W., Gorgels, J.P.M.C., Schouten, Y., Hoek, F.J. and Sanders, G.T. (1999) Independent prognostic value of C-reactive protein and troponin I in patients with unstable angina or non-Q-wave myocardial infarction. *Cardiovasc. Res.*, 42: 240-245.

Du Clos, T.W. (1989) C-reactive protein reacts with the U1 small nuclear ribonucleoprotein. J. *Immunol.*, 143: 2553-2559.

Du Clos, T.W., Mold, C., Paterson, P.Y., Alroy, J. and Gewurz, H. (1981) Localization of C-reactive protein in inflammatory lesions of experimental allergic encephalomyelitis. *Clin. Exp. lmmunol.*, 43: 565-573.

Finland, M. and Dowling, H.F. (1935) Cutaneous reactions and antibody response to intracutaneous injections of pneumococcus polysaccharides. *J. ImmunoL*, 29: 285-299.

Fletcher, T.C., White, A. and Baldo, B.A. (1980) Isolation of a phosphorylcholine-containing component from the turbot tapeworm, *Bothriocephalus scorpii* (Muller) and its reaction with C-reactive protein. *Parasite Immunol.*, 2: 237-248.

Gershov, D., Kim, S., Brot, N. and Elkon, K.B. (2000) C-reactive protein binds to apoptotic cells, protects the cells from assembly of the terminal complement components, and sustains an antiinflammatory innate immune response: implications for systemic autoimmunity. *J. Exp. Med*, 192: 1353-1363.

Gill et al., (2004) Human C-Reactive Protein Increases Cerebral Infarct Size After Middle Cerebral Artery Occlusion in Adult Rats, *J. Cerebral Blood Flow & Metabolism*, vol. 24 (No. 11), p. 1214-1218.

Gitlin, J.D., Gitlin, J.1. and Gitlin, D. (1977) Localisation of C-reactive protein in synovium of patients with rheumatoid arthritis. *Arthritis Rheum.*, 20: 1491-1499.

Griselli, M., Herbert, J., Hutchinson, W.L., Taylor, K.M., Sohail, M., Krausz, T. and Pepys, M.B. (1999) C-reactive protein and complement are important mediators of tissue damage in acute myocardial infarction. J. *Exp. Med.*, 190: 1733-1739.

Haverkate, F., Thompson, S.G., Pyke, S.D.M., Gallimore, J.R. and Pepys, M.B. (1997) Production of C-reactive protein and risk of coronary events in stable and unstable angina. *Lancet*, 349: 462-466.

Hawkins, P.N., Tennent, G.A., Woo, P. and Pepys, M.B. (1991) Studies in vivo and in vitro of serum amyloid P component in normals and in a patient with AA amyloidosis. *Clin. Exp. Immunol.*, 84: 308-316.

Hawkins, P.N., Wootton, R. and Pepys, M.B. (1990) Metabolic studies of radioiodinated serum amyloid P component in normal subjects and patients with systemic amyloidosis. *J. Clin. Invest.*, 86: 1862-1869.

Heuertz, R.M., Xia, D., Samols, D. and Webster, R.O. (1992) Transgenic mice expressing plasma rabbit C-reactive protein exhibit diminished vascular permeability and neutrophil infiltration in C5a-induced alveolitis. *FASEB J.*, 6: 1064 (abstract).

Hutchinson, W.L., Koenig, W., Frohlich, M., Sund, M., Lowe, G.D.O. and Pepys, M.B. (2000) Immunoradiometric assay of circulating C-reactive protein: age-related values in the adult general population. *Clin. Chem.*, 46: 934-938.

Kaplan, M.H. and Volanakis, J.E. (1974) Interaction of C-reactive protein complexes with the complement system. I. Consumption of human complement associated with the reaction of C-reactive protein with pneumococcal C-polysaccharide and with the choline phosphatides, lecithin and sphingomyelin. J. *ImmunoL*, 112: 2135-2147.

Kew, R.R., Hyers, T.M. and Webster, R.O. (1990) Human C-reactive protein inhibits neutrophil chemotaxis in vitro: possible implications for the adult respiratory distress syndrome. *J. Lab. Clin. Med*, 115: 339-345.

Kindmark, C.-O. (1972) In vitro binding of human C-reactive protein by some pathogenic bacteria and zymosan. *Clin. Exp. Immunol.*, 11: 283-289.

Kirkpatrick et al., Molecular Genetics, Structure and Function of C-reactive Protein, *Immunol. Res.* (1991) 10:43-53.

Koenig, W., Sund, M., Frohlich, M., Fischer, H.-G., Lowel, H., Doring, A., Hutchinson, W.L. and Pepys, M.B. (1999) C-reactive protein, a sensitive marker of inflammation, predicts future risk of coronary heart disease in initially healthy middle-aged men. Results from the MONICA (Monitoring Trends and Determinants in Cardiovascular Disease) Augsburg Cohort Study 1984 to 1992. *Circulation*, 99: 237-242.

Koizumi et al. (2000) Biologically Active Oligodeoxyribonucleotides. Part 12: N2-Methylation of 2'-deoxyguanosines Enhhances Stability of Parallel G-Quadruplex and anti-HIV 1 Activity, *Bioorganic & Medicinal Chem. Ltrs.*, vol. 10, pp. 2213-2216.

Kuller; L.H., Tracy, R.P., Shaten, J. and Meilahn, E.N. (1996) Relation of C-reactive protein and coronary heart-disease in the MRFIT nested case control study. *Am. J. Epidemiol.*, 144: 537-547.

Kushner, 1. and Kaplan, M.H. (1961) Studies of acute phase protein. I. An immunohistochemical method for the localization of Cx-reactive protein in rabbits. Association with necrosis in local inflammatory lesions. *J. Exp. Med*, 114: 961-973.

Kushner, I., Rakita, L. and Kaplan, M.H. (1963) Studies of acute phase protein. II. Localization of Cx-reactive protein in heart in induced myocardial infarction in rabbits. *J. Clin. Invest.*, 42: 286-292.

Lagrand, W.K., Niessen, H.W.M., Wolbink, G-J., Jaspars, L.H., Visser, C.A., Verheugt, F.W.A., Meijer, C.J.L.M. and Hack, C.E. (1997) C-reactive protein colocalizes with complement in human hearts during acute myocardial infarction. *Circulation*, 95: 97-103.

Liu et al. (1999) Positive Interaction Between 5-FU and FdUMP(10) in the Inhibition of Human Colorectal Tumour Cell Proliferation. *Antisense and Nucleic Acid Drug Development*, 9 :481-486. (Abstract).

Liuzzo, G., Biasucci, L.M., Gallimore, J.R., Grillo, R.L., Rebuzzi, A.G., Pepys, M.B. and Maseri, A. (1994) The prognostic value of C-reactive protein and serum amyloid A protein in severe unstable angina. *N. Engl. J. Med.*, 331: 417-424.

Lu et al., (1999) Synthetic Analogus of Irlbacholine: A Noval Antifungal Plant Metabolite Isolated from Irlbachia Alata *J. Natl. Prod., Am. Chem. Soc. And Am. Soc. of Pharmacognosy*, 62 : 824-828.

Mold, C. and Gewurz, H. (1980) Activation of the alternative pathway by liposomes: inhibitory effect of C-reactive protein. *Fed. Proc.*, 39: 702.

Mold, C. and Gewurz, H. (1981) Inhibitory effect of C-reactive protein on alternative C pathway activation by liposomes and *Streptococcus pneumoniae. J. Immunol.*, 127: 2089-2092.

Mold, C., Nakayama, S., Holzer, T.J., Gewurz, H. and Du Clos, T.W. (1981) C-reactive protein is protective against *Streptococcus pneumoniae* infection in mice. *J. Exp. Med.*, 154: 1703-1708.

Mold et al., (1999) Regulation of Complement Activation by C-Reactive Protein, *Immunopharmacology* 42 :23-30.

Mori et al., (1991) Involvements of Fibronectin and Lysophosphatidylcholine for Selective Binding of C-Reactive Protein, *Cell Mol. Biol.*, vol. 37 (No. 4), p. 421-431 (abstract only).

Morrow, D.A., Rifai, N., Antman, E.M., Weiner, D.L., McCabe, C.H., Cannon, C.P. and Braunwald, E. (1998) C-reactive protein is a potent predictor of mortality independently of and in combination with troponin T in acute coronary syndromes: a TIMI 11 A substudy. Thrombolysis in myocardial infarction. *J. Am. Coll. Cardiol.*, 31: 1460-1465.

Mortensen, R.F., Osmand, A.P., Lint, T.F. and Gewurz, H. (1976) Interaction of C-reactive protein with lymphocytes and monocytes: complement-dependent adherence and phagocytosis. *J. Immunol.*, 117: 774-781.

Nakayama, S., Mold, C., Gewurz, H. and Du Clos, T.W. (1982) Opsonic properties of C-reactive protein in vivo. *J. Immunol.*, 128: 2435-2438.

Narkates, A.J. and Volanakis, J.E. (1982) C-reactive protein binding specificities: artificial and natural phospholipid bilayers. *Ann. N. Y. Acad. Sci.*, 389: 172-182.

Nelson, S.R., Tennent, G.A., Sethi, D., Gower, P.E., Ballardie, F.W., Amatayakul-Chantler, S. And Pepys, M.B. (1991) Serum amyloid P component in chronic renal failure and dialysis. *Clin. Chim. Acta*, 200: 191-200.

Nikfardjam, M., Miillner, M., Schreiber, W., Oschatz, E., Exner, M., Domanovits, H., Laggner, AN and Huber, K. (2000) The association between C-reactive protein on admission and mortality in patients with acute myocardial infarction. *J. Intern. Med.*, 247: 341-345.

Osmand, A.P., Mortensen, R.F., Siegel, J. and Gewurz, H. (1975) Interactions of C-reactive protein with the complement system. III. Complement-dependent passive hemolysis initiated by CRP. *J. Exp. Med*, 142: 1065-1077.

Pepys, M.B. (1975) Studies in vivo of cobra factor and murine C3. *Immunology*, 28: 369-377.

Pepys, M.B. (1996) The acute phase response and C-reactive protein. In: *Oxford Textbook of Medicine, Third Ed.*, vol. 2 (Weatherall, D.J., Ledingham, J.G.G. and Warrell, D.A., eds.), Oxford University Press, Oxford, pp. 1527-1533.

Pepys et al. (2006) Targeting C-Reactive Protein for the Treatment of Cardiovascular Disease, *Nature*, vol. 440, pp. 1217-1221.

Pepys, M.B. and Baltz, M.L. (1983) Acute phase proteins with special reference to C-reactive protein and related protein (pentaxins) and serum amyloid A protein. *Adv. Immunol.*, 34: 141-212.

Pepys, M.B., Booth, S.E., Tennent, G.A., Butler, P.J.G. and Williams, D.G. (1994) Binding of pentraxins to different nuclear structures: C-reactive protein binds to small nuclear ribonucleoprotein particles, serum amyloid P component binds to chromatin and nucleoli. *Clin. Exp. Immunol.*, 97: 152-157.

Pepys, M.B., Dash, A.C., Fletcher, T.C., Richardson, N., Munn, E.A. and Feinstein, A. (1978) Analogues in other mammals and in fish of human plasma proteins C-reactive protein and amyloid P component. *Nature*, 273: 168-170.

Pepys, M.B., Rowe, I.F. and Baltz, M.L. (1985) C-reactive protein: binding to lipids and lipoproteins. *Int. Rev. Exp. Pathol.*, 27: 83-111.

Pepys, M.B., Tompkins, C. and Smith, A.D. (1979) An improved method for the isolation from *Naja naja* venom of cobra factor (CoF) free of phospholipase A. *J. Immunol. Methods*, 30: 105-117.

Pietila, K.O., Harmoinen, A.P., Jokinftty, J. and Pasternack, A.I. (1996) Serum C-reactive protein concentration in acute myocardial infarction and its relationship to mortality during 24 months of follow-up in patients under thrombolytic treatment. *Eur. Heart J.*, 17: 1345-1349.

Ridker, P.M. (1998) C-reactive protein and risks of future myocardial infarction and thombotic stroke. *Eur. Heart J*, 19: 1-3.

Ridker, P.M., Buring, J.E., Shih, J., Matias, M. and Hennekens, C.H. (1998) Prospective study of C-reactive protein and the risk of future cardiovascular events among apparently healthy women. *Circulation*, 98: 731-733.

Ridker, P.M., Cushman, M., Stampfer, M.J., Tracy, R.P. and Hennekens, C.H. (1997) Inflammation, aspirin, and the risk of cardiovascular disease in apparently healthy men. *N. Engl. J. Med*, 336: 973-979.

Ridker, P.M., Cushman, M., Stampfer, M.J., Tracy, R.P. and Hennekens, C.H. (1998) Plasma concentration of C-reactive protein and risk of developing peripheral vascular disease. *Circulation*, 97: 425-428.

Shine, B., de Beer, F.C. and Pepys, M.B. (1981) Solid phase radioimmunoassays for C-reactive protein. *Clin. Chim. Acta*, 117: 13-23.

Shrive, A.K., Cheetham, G.M.T., Holden, D., Myles, D.A.A., Turnell, W.G., Volanakis, J.E., Pepys, M.B., Bloomer, A.C. and Greenhough, T.J. (1996) Three- dimensional structure of human C-reactive protein. *Nature Struct. Biology*, 3: 346- 354.

Steel et al., The Major Acute Phase Reactants: C-reactive protein, serum amyloid P component and serum amyloid A protein, *Immunology Today* (1994) 15:81-89.

Thompson, D., Pepys, M.B. and Wood, S.P. (1999) The physiological structure of human C-reactive protein and its complex with phosphocholine. *Structure*, 7: 169-177.

Tommasi, S., Carluccio, E., Bentivoglio, M., Buccolieri, M., Mariotti, M., Politano, M. and Corea, L. (1999) C-reactive protein as a marker for cardiac ischemic events in the year after a first, uncomplicated myocardial infarction. *Am. J. Cardiol.*, 83: 1595-1599.

Torzewski, J., Torzewski, M., Bowyer, D.E., Frohlich, M., Koenig, W., Waltenberger, J., Fitzsimmons, C. and Hombach, V. (1998) C-reactive protein frequently colocalizes with the terminal complement complex in the intima of early atherosclerotic lesions of human coronary arteries. *Arterioscler. Thromb. Vasc.* Biol., 18: 1386-1392.

Tsujimoto et al., (1980) C-Reactive Protein Induced Agglutination of Lipid Suspensions Prepared in the Presence and Absence of Phosphatidylcholine, *J. Biochem.*, vol. 87 (No. 5), p. 1531-1537 (abstract only).

Ueda, S., Ikeda, U., Yamamoto, K., Takahashi, M., Nishinaga, M., Nago, N. and Shimada, K. (1996) C-reactive protein as a predictor of cardiac rupture after acute myocardial infarction. *Am. Heart J*, 131: 857-860.

Vadas et al., (1995) Inhibition of Human Group II phospholipase A2 by C-reactive Protein in vitro, *J. Lipid Mediat. Cell Signal*, vol. II (No. 2), p. 187-200 (abstract only).

van Leeuwen, M.A., van Rijswijk, M.H., Sluiter, W.J., van Riel, P.L.C.M., Kuper, I.H., van de Putte, L.B.A., Pepys, M.B. and Limburg, P.C. (1997) Individual relationship between progression of radiological damage and the acute phase response in early rheumatoid arthritis. Towards development of a decision support system. *J. Rheumatol.*, 24: 20-27.

Vigushin, D.M., Pepys, M.B. and Hawkins, P.N. (1993) Metabolic and scintigraphic studies of radioiodinated human C-reactive protein in health and disease. *J. Clin. Invest.*, 91: 1351-1357.

Volanakis, J.E. (1982) Complement activation by C-reactive protein complexes. *Ann. N. Y. Acad Sci.*, 389: 235-250.

Volanakis, J.E. and Kaplan, M.H. (1971) Specificity of C-reactive protein for choline phosphate residues of pneumococcal C-polysaccharide. *Proc. Soc. Exp. Biol. Med*, 136: 612-614.

Volanakis, J.E. and Kaplan, M.H. (1974) Interaction of C-reactive protein complexes with the complement system. II. Consumption of guinea-pig complement by CRP complexes: requirement for human Clq. *J. Immunol.*, 113: 9-17.

Volanakis, J.E. and Wirtz, K.W.A. (1979) Interaction of C-reactive protein with artificial phosphatidylcholine bilayers. *Nature*, 281: 155-157.

Wang et al. (1999) Synthesis and Properties of a Bipolar, Bisphosphatidyl Ethanolamine that Forms Stable 2-Dimensional Self-Assembled Bilayer Systems and Liposomes, *J. Org. Chem., American Chemical Society*, 64 : 4140-4147.

Weiser, J.N., Pan, N., McGowan, K.L., Musher, D., Martin, A. and Richards, J. (1998) Phosphorylcholine on the lipopolysaccharide of

*Haemophilus influenzae* contributes to persistence in the respiratory tract and sensitivity to serum killing mediated by C-reactive protein. *J. Exp. Med*, 187: 631-640.

Wolbink, G.-J., Bossink, A.W.J., Groeneveld, A.B.J., de Groot, M.C.M., Thijs, L.G. and Hack, C.E. (1998) Complement activation in patients with sepsis is in part mediated by C-reactive protein. *J. Infect. Dis.*, 177: 81-87.

Yother, J., Volanakis, J.E. and Briles, D.E. (1982) Human C-reactive protein is protective against fatal *Streptococcus pneumoniae* infection in mice. *J. Immunol.*, 128: 2374-2376.

Zhang, YX, Cliff, W.J., Schoefl, G.I. and Higgins, G. (1999) Coronary C-reactive protein distribution: its relation to development of atherosclerosis. *Atherosclerosis*, 145: 375-379.

\* cited by examiner

TREATMENT AND PREVENTION OF TISSUE DAMAGE

This is a U.S. national stage of Intl. Patent Appl. No. PCT/GB03/02096, filed 14 May 2003, which claims priority to Great Britain Patent Appl. No. 0211136.7, filed 15 May 2002.

FIELD OF THE INVENTION

The present invention relates to a method for the treatment or prevention of tissue damage in a subject, especially a human subject having an inflammatory and/or tissue damaging condition. Compounds are provided for the treatment or prevention of such tissue damage by virtue of their capacity to inhibit binding of C-reactive protein (CRP) to autologous and extrinsic ligands in vivo.

BACKGROUND TO THE INVENTION

C-reactive protein (CRP) is a normal plasma protein of the pentraxin protein family, the other member of which is the very closely similar molecule, serum amyloid P component (SAP)(1). CRP is the classical acute phase protein, the circulating concentration of which increases dramatically in response to most forms of inflammation, tissue injury and infection, and the value attained in most conditions correlates closely with the extent and activity of disease(2). CRP is a calcium dependent ligand binding protein, the ligand which it binds with highest affinity being phosphocholine residues(3), but it also binds a variety of other ligands. It binds many of its ligands with high avidity. Known ligands for CRP include both autologous and extrinsic structures. Autologous ligands include native(4,5) and modified plasma lipoproteins, damaged cell membranes (6), a number of different phospholipids and related compounds(7), and small nuclear ribonucleoprotein particles(8,9). Extrinsic ligands include many glycan, phospholipid and other components of micro-organisms, such as capsular and somatic components of bacteria, fungi and parasites, as well as plant products(10-15). When CRP has bound to its ligands it becomes capable of activating complement by the classical pathway via Clq(16-19) and achieving activation and fixation of C3, the main adhesion molecule of the complement system(20,21), as well as engagement of the terminal lytic phase, C5-C9(22).

Whilst very early clinical work(23) suggested that CRP might possibly contribute to inflammation, and subsequent experimental animal studies were interpreted as showing a pro-inflammatory role for CRP, there has until lately been no direct evidence of any involvement of CRP in processes of inflammation and tissue damage. There are a few reports of CRP deposition in inflammatory and necrotic tissue lesions, and of association between CRP and complement activation (24-30). However none of these studies shows directly that CRP is responsible for tissue damage, and the only study of real time CRP deposition in human tissues in living patients showed that it occurred only in trace amounts, if at all(31). Indeed the published work that directly examines the role of CRP in experimental models of disease indicates that CRP may have an anti-inflammatory role that down-regulates infiltration of inflammatory cells and reduces tissue damage(32, 33). This would be consistent with the finding that complexed CRP is relatively inefficient at generating the terminal phase of complement activation and that involvement of CRP down-regulates other potentially inflammatory aspects of complement activation(34,35). Very recent work in different models involving handling of apoptotic cells also indicates that CRP has anti-inflammatory properties(36). There is thus certainly no consensus about the role of CRP in vivo and the predominant view is that it may be anti-inflammatory. In general the association of increased CRP production with disease conditions has hitherto been interpreted on the basis that CRP production reflects the severity of the underlying disease and/or the presence of intercurrent complications. However we have lately demonstrated unequivocally that CRP can exacerbate ischaemic tissue damage in vivo, via a complement dependent mechanism, and established that inhibition of CRP binding in vivo is a potentially important therapeutic goal (37). This is the subject of U.S. patent application Ser. No. 0119370.5, the contents of which are hereby incorporated by reference.

Atherosclerosis is extremely prevalent in developed countries and its major complications of myocardial infarction and stroke together account for about one third of all deaths. Although there have been advances in understanding of some aspects of pathogenesis and in prophylactic and post-event salvage treatments, the personal, social and economic burden of these conditions remains enormous. Similarly, chronic inflammatory diseases of unknown aetiology are common, debilitating, expensive and often dangerous to treat symptomatically, as well as being incurable and often shortening life expectancy. For example, rheumatoid arthritis affects about 4% of the population over the age of 50 years and, as well as being painful and causing severe disability, it is associated with significant premature mortality. The cancer burden is very heavy, accounting for about one third of all deaths in developed countries, and the severity and importance of infectious disease throughout the world is evident. There is a pressing need for new drugs to reduce severity and to prolong survival in all these different conditions.

SUMMARY OF THE INVENTION

Accordingly, in a first aspect, the present invention provides an agent for use in medicine, particularly for the preparation of a composition for the treatment or prevention of tissue damage in a subject having an inflammatory and/or tissue damaging condition. The agent comprises a plurality of ligands covalently co-linked so as to form a complex with a plurality of C-reactive protein (CRP) molecules in the presence thereof. At least two of the ligands are the same or different and are capable of being bound by ligand binding sites present on the CRP molecules. Alternatively, at least one of the ligands is capable of being bound by a ligand binding site present on a CRP molecule, and at least one other of the ligands is capable of being bound by a ligand binding site present on a serum amyloid P (SAP) molecule.

Surprisingly, it has been found that agents according to the present invention are potent in inhibiting ligand binding to CRP. It has been shown that CRP plays a direct pathogenetic role in a disease condition, specifically by enhancing the extent of myocardial damage produced by ischaemic injury. This pathogenetic role can be treated or prevented by the use of a drug capable of inhibiting the binding of CRP to its target ligand in vivo. Without wishing to be bound by theory and as described in further detail herein, it is thought that the inhibition of binding of CRP to its target ligand in vivo would prevent CRP from activating complement and thereby reduce or eliminate the deleterious effects of CRP mediated complement activation now thought responsible for tissue damage in the conditions to be treated according to the present invention.

In one embodiment according to the invention, the inflammatory and/or tissue damaging condition comprises atherosclerosis.

Whilst CRP is produced in large amounts in response to most forms of tissue injury, inflammation and infection, its circulating concentration is extremely low in normal healthy subjects and in most individuals in the general population(38, 39). Until recently these low levels were not considered to be of any clinical significance and the generally available assays for CRP were designed only to detect and measure circulating CRP when the concentration exceeded 5 or even 10 mg/l, representing the 90-99$^{th}$ centile of the range found in healthy subjects. However a large body of work has accumulated since our original discoveries, starting in 1994(40), that shows convincingly that even within the reference range for CRP, among values previously considered to be "normal", increased production of CRP is very significantly associated with atherothrombotic events, including myocardial infarction, stroke and progression of vascular disease(41-49).

The mechanisms underlying the association between even modestly increased CRP production and development, progression and complications of atherosclerosis, are not known. However it is likely to be highly relevant that atherosclerosis is known to be an inflammatory condition, and that CRP and activated complement are co-deposited in virtually all atheromatous plaques(29,50). Furthermore, CRP selectively binds to low density lipoprotein (LDL), the major lipoprotein that accumulates in the arterial lesions of atherosclerosis(4,5), and binding of CRP to "modified", that is partly degraded, LDL such as is found in the plaques, potently activates complement (51). CRP promotes uptake of native LDL by macrophages and vascular smooth muscle cells in vitro to form foam cells, that are typical and important pathological features of atherosclerotic lesions in vivo. Finally there is evidence that CRP can stimulate macrophages, which are the most abundant cells infiltrating atheromatous plaques, to produce tissue factor (TF)(52). TF is the initiator of blood coagulation responsible for initiation of the thrombus formation on ruptured plaques that actually occludes atherosclerotic arteries and precipitates myocardial infarction or stroke. CRP may thus directly contribute to the pathogenesis, progression and clinically significant complications of atherosclerosis.

Once myocardial infarction has occurred, all patients mount a major acute phase response of CRP and the peak value attained is very significantly prognostic of outcome, that is complications and death, over the ensuing days, weeks and months (53-59). Given the universal co-deposition of CRP and activated complement within the infarct itself, this strongly suggests that CRP contributes importantly to the extent and severity of the ischaemic pathology(28,60,61). CRP values, and particularly cumulative production of CRP over time, are also very significantly predictive of progression, severity and complications of chronic inflammatory diseases of unknown aetiology, such as rheumatoid arthritis (62) and Crohn's disease, of acute and chronic bacterial, viral, fungal and parasitic infections, of ischaemic and necrotic diseases such as acute pancreatitis, and of many forms of cancer (reviewed in (1,2)). Even in the context of elective surgery, pre-operative CRP values and post-operative CRP production predict complications and outcome(63). Our observations in atherosclerosis, and especially in the rat model of myocardial infarction exacerbated by human CRP, now indicate that CRP may actually be actively contributing to disease severity in all these different conditions In a further embodiment, the inflammatory and/or tissue damaging condition is selected from an infection, an allergic complication of infection, an inflammatory disease, ischaemic or other necrosis, traumatic tissue damage and malignant neoplasia.

For example, where the condition is an infection, this may be a non-protozoal infection such as a bacterial or viral infection. Where the condition is an allergic complication of infection, this may be selected from rheumatic fever, glomerulonephritis and erythema nodosum leprosum. Where the condition is an inflammatory disease, this may be selected from rheumatoid arthritis, juvenile chronic (rheumatoid) arthritis, ankylosing spondylitis, psoriatic arthritis, systemic vasculitis, polymyalgia rheumatica, Reiter's disease, Crohn's disease and familial Mediterranean fever. Where the condition involves ischaemic or other necrosis selected from myocardial infarction, ischaemic stroke, tumour embolization and acute pancreatitis. Where the condition is traumatic, this may be selected from acute or elective surgery, burns, chemical or physical injury, and fractures. Where the condition is malignant neoplasia, this may be selected from lymphoma, Hodgkin's disease, carcinoma and sarcoma.

According to the present invention, drugs that either inhibit the binding of CRP to its ligands in vivo, and/or that reduce its availability for such binding in vivo, will block the contribution of CRP to pathogenesis of disease and will thereby reduce extent and severity of disease, reducing symptoms and prolonging survival. The present invention provides compounds with such effects, for the preparation of a composition for the prevention and/or treatment of atherosclerosis and its complications, including myocardial infarction, stroke and peripheral vascular disease, acute and chronic inflammatory diseases of known and unknown aetiology, acute and chronic infections of all types, traumatic injuries including burns, acute and elective surgery, malignant neoplasia of all types, and all disease conditions associated with increased CRP production.

In the agents of the present invention, although the ligands may be directly linked together by a covalent bond, the ligands are preferably covalently co-linked by a linker. This enables the ligands to be sufficiently spatially separated whereby a plurality of target proteins may be bound to the agent without one protein hindering the binding of the other protein or proteins. The exact structure of the linker is not critical although it is typically preferred not to include reactive groups. The linker may comprise a linear or branched hydrocarbylene which may have one or more of its carbon atoms optionally substituted by a heteroatom. The linker may have a chain length in the range 2 to 20 atoms although a preferred range is 5 to 7 atoms. Useful chain length and chemical composition may be determined empirically depending on the proteins with which the agent is to be complexed. Where the agent has two ligands, the linker is typically linear; a preferred general structure is ligand-linker-ligand. This is conveniently denoted a "palindrome" for the purposes of the present application. The linker may comprise one or more double bonds, as discussed in further detail below. Where the linker comprises at least two double bonds these may be conjugated and are preferably trans to one another. Alternatively, the linker comprises one or more arylene groups, for example as —Ar—Ar— moiety. The arylene groups may be heteroarylene groups. Preferably, the arylene groups are

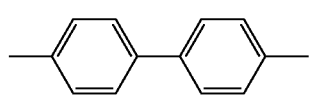

Other structures involving three, four or more ligands with an appropriate branched chain linker are also contemplated where three, four or more target proteins could form a complex. For example, the linker may comprise a cyclic core substituted on one face thereof by a plurality of substituent groups each comprising a ligand capable of being bound by ligand binding sites present on CRP and substituted on the other face thereof by a ligand capable of being bound either by ligand binding sites present on CRP or by ligand binding sites present on SAP.

The ligand used in the agent of the present invention may be selected from the ligands known to be bound by the CRP ligand binding site, ligands predicted to be bound by that site, for example on the basis of structural information available on the binding site such as X-ray crystallographic information, or structural analogues thereof. Suitable compounds can be identified by high throughput screening of chemical libraries and/or structure based molecular design. The affinity of each individual ligand-CRP binding site interaction does not need to be particularly high provided that the ligand is specific for each target protein. It is possible that a dissociation constant of up to 10 millimolar would suffice. However, it is preferred that the dissociation constant is no more than 1 millimolar, more preferably less than 100 micromolar, most preferably less than 10 micromolar. The affinity is preferably about micromolar or higher. Micromolar affinity has been found to be sufficient in the case of CRP, although the highest possible affinity is clearly desirable.

In a further aspect, the present invention provides a method for selecting a pharmaceutical compound for treating or preventing tissue damage in a subject having an inflammatory and/or tissue damaging condition, which comprises contacting C-reactive protein (CRP) with a test ligand thereof under conditions to permit CRP ligand binding, in the presence of a test compound; and selecting the test compound as the pharmaceutical compound if the test compound inhibits binding of CRP to the test ligand. The test compound comprises a plurality of ligands which are the same or different and which are covalently co-linked so as to form a complex with a plurality of CRP molecules.

The present invention further provides a process for the production of a pharmaceutical agent. This process comprises (1) identifying a pharmaceutical compound by selecting the compound as described above; and (2) producing a pharmaceutical agent by providing a pharmaceutical compound or a pharmaceutical-acceptable derivative thereof.

The present invention is therefore concerned with a method for selecting a pharmaceutical compound which includes testing for CRP ligand binding in the presence of a test compound. Any test compound which inhibits binding of CRP to the test ligand is selected as a potential pharmaceutical. For example, the test compound may be selected in the sense that it is identified and can then be produced on a larger scale by chemical or biochemical synthesis or may be physically selected for direct formulation as a pharmaceutical. In accordance with the process for production of the pharmaceutical agent, the test compound may be formulated for pharmaceutical use or may be derivatised or chemically modified to produce a pharmaceutically-acceptable derivative thereof. Such derivatisation may simply be required to incorporate new functional groups or alter existing functional groups to make the agent easier to formulate, for example by altering the solubility of the compound. Derivatisation of this nature may be used to decrease the toxicity of the compound, to alter the stability of the compound or even to modify the pharmacological activity thereof. Any such derivatised or modified compound may need to be retested according to the method of the present invention. This process can equally be applied to the agent of the present invention in order to improve its pharmaceutical properties.

In the step of contacting CRP with the test ligand, the conditions must be sufficient to permit CRP ligand binding in the absence of the test compound. In this way, where CRP ligand binding does not occur in the presence of the test compound, or occurs to a smaller extent than expected, this effect can be attributed to the test compound. It should be noted here that inhibition of binding should be broadly construed and is not limited to any particular mechanism; any reduction of the extent of binding constitutes inhibition of binding according to the present invention. Inhibition of binding is generally measured with reference to a control value (maximum binding in absence of test compound) and it is preferred that the $IC_{50}$ be low micromolar or less, more preferably nanomolar or less. Contacting takes place under conditions which include sufficient free calcium ions to permit the specific calcium dependent binding of CRP. A preferred buffer for the contacting is physiological buffered saline. CRP may be provided in pure or isolated form or incorporated in whole serum.

The order in which the CRP, test ligand and test compound are contacted together is not critical. All three components can be mixed at essentially the same time or two of the three components can be mixed and perhaps pre-incubated before addition of the third component. Contacting generally takes place under conditions in which at least one of the components is in the liquid phase. It is convenient, however, for either the CRP or the test ligand to form part of a solid phase so that, in the testing procedure, phase separation can be used as a technique to separate bound species from unbound species to facilitate testing for the extent of CRP ligand binding.

Accordingly, it is preferred that a first component comprising one of CRP or the test ligand is present as part of a solid phase, which is contacted with a second component comprising the other as part of a liquid phase. The step of testing for CRP ligand binding may then comprise detecting binding of the second component to the solid phase. Detecting binding of the second component to the solid phase may be effected either by detecting the presence of the second component on the solid phase or by determining the amount of second component unbound to the solid phase and deducing from the amount of second component originally applied to the solid phase the amount actually binding to the solid phase.

According to this embodiment, the solid phase preferably comprises the first component attached to a solid support, which solid support may comprise a particulate support or a solid surface. In a convenient embodiment, the solid surface comprises an interior surface of the container such as a microtitre plate well.

Conveniently, the step of testing for CRP ligand binding further comprises washing the solid phase to remove unbound material.

The second component may be labelled with a detectable label such as a radiolabel, a fluorochrome or an enzyme, as discussed herein. Alternatively, the binding of the second component to the solid phase may be detected immunologically either by antibody binding to the second component as bound to the solid phase or by quantitative immunological determination of the amount of second component not bound to the solid phase.

The present invention provides in vitro spot tests, low throughput, and high throughput screening procedures for detecting compounds with the capacity to inhibit binding of CRP, from man or other animals, to any and all of its known biological and chemical ligands. These methods are suitable for screening compound libraries of natural compounds of organic, inorganic and biological origin, as well as chemical libraries created by conventional synthesis or any form of combinatorial chemistry. They are also suitable for analysis of the mechanism of inhibition of CRP binding, and for evaluation of potency of inhibition during chemical and medicinal chemistry development of potential or actual pharmaceutical products from lead compounds identified by screening or spot testing. The present invention also comprises in vivo methods for testing effects and potency of CRP-inhibitory compounds on CRP binding, plasma turnover and catabolism in man and experimental animals, and on experimental models of disease that are exacerbated by human CRP.

Accordingly, in a further aspect, the present invention provides a method for selecting a pharmaceutical compound for treating or preventing tissue damage from a plurality of test compounds which comprises providing an array of reaction zones and a plurality of test compounds, and selecting the pharmaceutical compound by performing the above method of selecting the compound in each reaction zone.

In a preferred embodiment, each ligand of the agent according to the present invention independently has the general formula

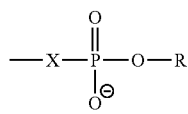

in which X is O or $CH_2$—$CH_2$ and R comprises an amine. In the present context, the amine may be a primary, secondary or tertiary amine, or a quarternary ammonium. The amine may be aliphatic or aromatic, including heterocyclic compounds in which the nitrogen group is part of a ring. The amine may be linked to the —O— by an alkylene group such as a methylene or ethylene group, which groups may optionally be substituted with a substituent such as a 3 hydroxy,1-cyclopentanyl or 4 hydroxy,1-cyclohexanyl substituent. Preferably, the amine comprises a trimethylammonium, an amino methyl dimethyl ammonium or $NH_2$. Examples of these ligands are presented below as compounds 2, 3, 7 and 8 and are discussed in further detail in the Examples. In a particularly preferred embodiment, each ligand comprises a [(trimethylammonium)ethoxyl phosphinyl]oxy group. In this way, the agent preferably comprises 1,6-bis[{[(trimethylammonium)ethoxy]phosphinyl}-oxy]hexane, colloquially phosphocholine-hexane-phosphocholine, abbreviated here as PCHPC. Examples of these ligands are presented below as compounds 2, 3, 7 and 8 and are discussed in further detail in the Examples.

In a further embodiment, the amine may comprise an indole, adenine or guanine. Examples of such ligands are presented in the Examples as compound nos. 1, 5 and 6.

Pharmaceutical compositions may be formulated comprising an agent according to the present invention optionally incorporating a pharmaceutically-acceptable excipient, diluent or carrier. The pharmaceutical compositions may be in the form of a prodrug comprising the agent or a derivative thereof which becomes active only when metabolised by the recipient. The exact nature and quantities of the components of such pharmaceutical compositions may be determined empirically and will depend in part upon the route of administration of the composition. Routes of administration to recipients include oral, buccal, sublingual, by inhalation, topical (including ophthalmic), rectal, vaginal, nasal and parenteral (including intravenous, intra-arterial, intra-muscular, subcutaneous and intra-articular) For convenience of use, dosages according to the present invention are preferably administered orally but this will depend on the actual drug and its bioavailability.

BRIEF DESCRIPTION OF THE DRAWINGS

The invention will now be described in further detail, by way of example only and with reference to the accompanying drawings and the following Examples.

FIG. 2 shows a visualisation of pairs of CRP molecules cross-linked by PCHPC, in which

DETAILED DESCRIPTION OF THE INVENTION

Examples

Figure 1:
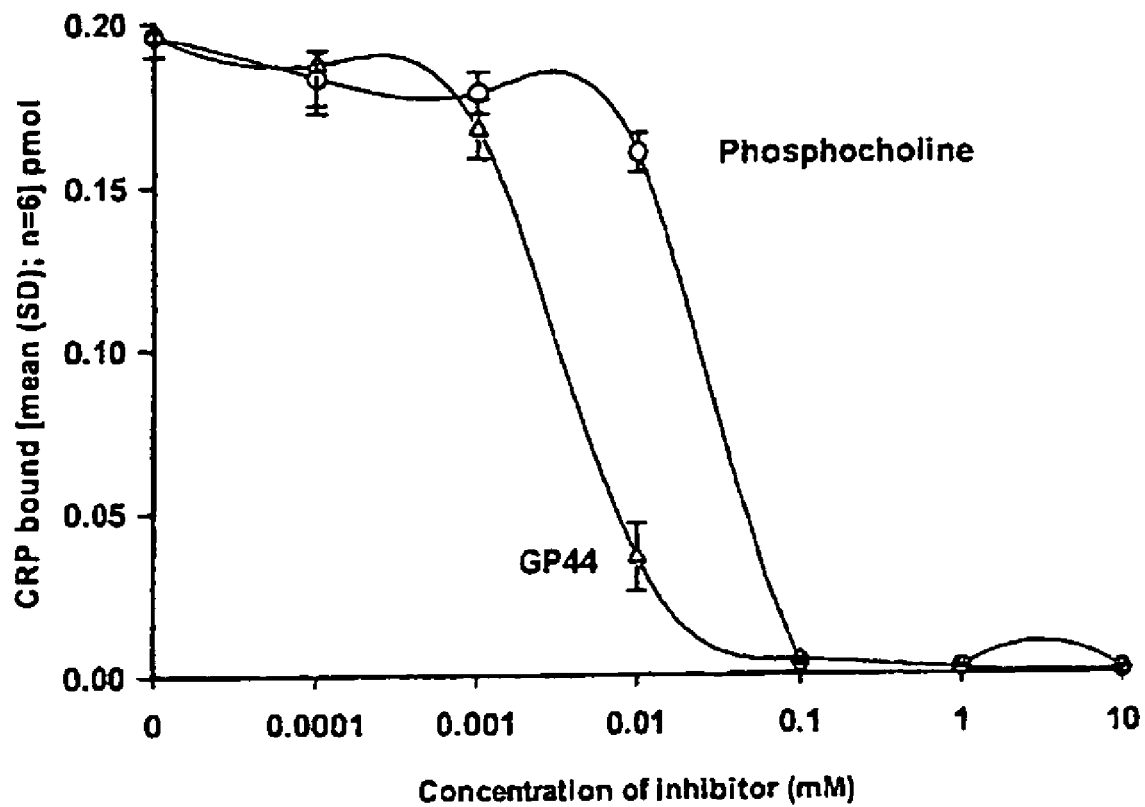
FIG. 1 shows inhibition of CRP binding to immobilised CPS by phosphocholine and PCHPC (lot number GP44), showing 10 fold lower $IC_{50}$ for PCHPC than phosphocholine.

The physiological moiety bound by CRP with greatest affinity is phosphocholine that is a component of some of the extrinsic and some of the autologous macromolecular ligands of CRP. According to one embodiment of the present invention, bis-phosphocholine molecules comprising two phosphocholine head groups joined by a linker structure, are potent inhibitors of CRP binding to all of its ligands, both in vitro and in vivo. A typical example of this invention is 1, 6-bis[{[(trimethylammonium)ethoxy]phosphinyl}-oxy]hexane, colloquially phosphocholine-hexane-phosphocholine, abbreviated here as PCHPC. The structure and a typical synthesis of this molecule are as shown below.

1,6-Bis[{[(trimethylammonium)ethoxy]phosphinyl}-oxy]hexane

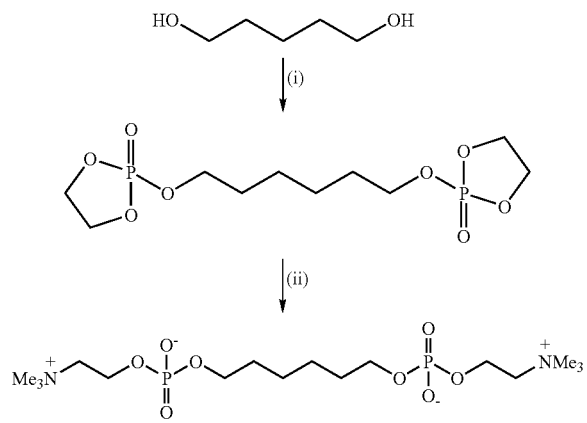

Reagents and Conditions:
(i) ethylene chlorophosphate, K₂CO₃, DCM/THF, −10° C. to RT, 6 h
(ii) MeCN, Me₃N, 100° C. (microwave heating), sealed tube, 30 mins.

Ethylene chlorophosphate (19.34 mL, 0.212 mol) was added dropwise to a stirring suspension of anhydrous potassium carbonate (29.84 g, 0.216 mol) in freshly distilled dichloromethane (50 mL) at −10° C. under an atmosphere of argon. A solution of hexane 1,6-diol (5 g, 42.34 mmol) in freshly distilled tetrahydrofuran (10 mL) was added dropwise to this mixture over 10 minutes, and the resultant suspension was stirred at −10° C. The reaction was warmed to 25° C. over a period of 4 h. After 6 h, t.l.c. indicated the presence of a major compound and no starting material. The reaction mixture was diluted with dichloromethane (250 mL), filtered and poured into pH 7 buffer solution (200 mL). The organic layer was washed with saturated sodium hydrogen carbonate solution (200 mL) and the aqueous layers extracted with dichloromethane (100 mL) and chloroform (100 mL). The combined organic layers were dried (MgSO₄), filtered (solvent: dichloromethane) and concentrated in vacuo to yield the *bisphosphate ester* as a pale yellow oil. This oil (circa 9 g) was dissolved in anhydrous acetonitrile (60 mL) and distributed between 30 Smith Process Vials™ (5 mL capacity). Trimethylamine (2 mL, −10° C.) was added to each vessel before the vials were sealed and heated to 100° C. for 30 minutes under microwave irradiation (300 W). After cooling, the vials were vented (caution!), combined (solvent: methanol), concentrated in vacuo and dried exhaustively under high vacuum to afford 1,6-bis[{[(trimethylammonium)ethoxy]phosphinyl}-oxy]hexane, as a pale yellow foam (11.8 g).

General experimental procedures. Microwave heating experiments were performed on a Personal Chemistry Smith Synthesizer in dedicated glassware (available from Personal Chemistry, Uppsala, Sweden). Analytical thin layer chromatography was performed on precoated glass-backed plates (Merck Kieselgel 60 F254). Visualization was accomplished with an aqueous solution of ammonium molybdate or potassium permanganate, followed by heating. All moisture and/or air sensitive reactions were conducted in oven-dried (150° C.) glassware under an inert atmosphere of argon. Acetonitrile and dichloromethane were distilled from calcium hydride. Tetrahydrofuran was distilled from sodium in the presence of benzophenone. Other reagents and solvents were used as supplied or purified using standard procedures. Buffer pH 7 was prepared by dissolving potassium dihydrogen orthophosphate (212.5 g) and sodium hydroxide (36.25 g) in water (2375 ml).

An improved synthetic procedure is described below.

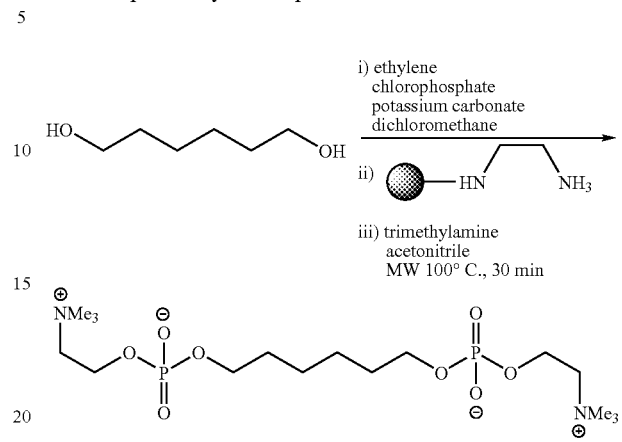

Ethylene chlorophosphate (15.1 g, 106 mmol, 5 eq) was added drop-wise to a stirring suspension of anhydrous potassium carbonate (14 g, 107.6 mmol, 5.1 eq) in freshly distilled dichloromethane (20 mL) at −10° C. under an atmosphere of argon. A solution of 1,6-hexanediol (2.5 g, 22 mmol) in freshly distilled tetrahydrofuran (10 mL) was added dropwise to this mixture over 10 minutes and the resultant suspension was stirred at −10° C. The reaction was warmed to 25° C. over a period of 4 h. After 16 h, the reaction appeared complete by LC-MS. To the reaction mixture was added N-(2-Aminoethyl)-aminoethyl polystyrene resin (ca. 22 g of a 2.8 mM/g loaded polymer, equivalent to 62 mmol of theoretical unreacted ethylene chlorophosphate) and the resulting mixture stirred at 20° C. for 15 mins. After this time, the mixture was filtered through a sinter funnel and the filtrate was evaporated to yield the biphosphate ester as a pale yellow oil (quantitative). Some of this oil (ca. 4 g) was dissolved in anhydrous acetonitrile (40 ml) and distributed between 20 Smith Process Vials™ (5 mL capacity). Cold, condensed, trimethylamine (2mL) was added to each vial before the vials were sealed and heated to 100° C. for 30 mins under microwave irradiation (300 W) After cooling, the vials were vented (caution!) and the supernatants combined. The residue left at the bottom of each vial was dissolved in methanol and combined with the supernatants which were evaporated and dried exhaustively under high vacuum to yield 1,6-bis[{[(trimethylammonium)ethoxy]phosphinyl}-oxy]hexane as a pale yellow foam (6 g, quantitative). 1H NMR (400 MHz, MeOD): 4.27 (2H, br, CH₂C$\underline{H}$₂N), 3.89 (2H, m, C$\underline{H}$₂CH₂N), 3.65 (2H, br, C$\underline{H}$₂OP(O)O₂CH₂CH₂N), 3.24 (9H, s, N(C$\underline{H}$₃)₃), 1.65 (2H, br, CH₂C$\underline{H}$₂CH₂OP), 1.45 (2H, br, C$\underline{H}$₂CH₂CH₂OP).

The potent capacity of PCHPC to inhibit binding in vitro of CRP to its best known extrinsic macromolecular ligand, pneumococcal somatic C-polysaccharide (CPS), is illustrated in FIG. 1. CPS was covalently immobilised on plastic microtitre plates and typical calcium-dependent binding to it of $^{125}$I-labelled pure human CRP was readily demonstrable. This binding was clearly inhibited by phosphocholine itself in solution, with an IC$_{50}$ of about 20 μM, whilst, in contrast, PCHPC inhibited CRP binding with a tenfold lower IC$_{50}$ of about 2 μM (FIG. 1). Furthermore direct measurement by isothermal microcalorimetry of the K$_d$ for PCHPC with CRP gave values in replicate experiments of 0.469, 0.679, 0.73 and 0.855 μM, compared to values for K$_d$ of phosphocholine with CRP of 1.6, 2.02 and 3.8 μM.

The greater potency of PCHPC as a ligand for, and an inhibitor of, CRP binding, compared to free phosphocholine itself, reflects the bifunctional, palindromic, nature of the PCHPC molecule. The presence at each end of the linker moiety of a phosphocholine residue, recognised and able to be bound by the ligand binding pocket present in each protomer of the pentameric CRP molecule, enables PCHPC to bridge across and cross link pairs of CRP molecules. This capacity for multiple interactions greatly enhances the avidity of the interaction between PCHPC and CRP. The ligand binding sites on each of the 5 protomers in the CRP molecule are all on the same face of the disc-like pentameric assembly of the native protein. Cross linking of pairs of CRP molecules by PCHPC molecules also thus further reduces availability of CRP for binding to other ligands by occluding the binding or 'B' face of the protein. In overwhelming molar excess of PCHPC, every ligand binding site on CRP is occupied by an individual PCHPC molecule, no cross linking of pairs of CRP molecules can occur, and therefore the CRP remains in its native single pentameric form. Free phosphocholine is bound by CRP but being 'monomeric' it cannot cross link pairs of CRP molecules. These effects are shown by molecular sieve chromatography that distinguishes clearly between the native single pentameric assembly of CRP and the pairs of such pentamers that have been dimerised by the drug. Importantly with respect to the capacity of PCHPC to act as an inhibitor of potentially pathogenic CRP binding in vivo, the same effects are observed with isolated pure CRP in aqueous buffer and with CRP in the physiological milieu of whole serum.

TABLE

Effect of PCHPC on molecular assembly of CRP revealed by gel filtration chromatography

| Molar excess of PCHPC or free phosphocholine | Molecular assembly of CRP |
| --- | --- |
| No drug | Single pentamers |
| Equimolar PCHPC | Decameric dimers |
| 10 fold excess of PCHPC | Decameric dimers |
| 10 fold excess of phosphocholine | Single pentamers |
| 1,000 fold excess of PCHPC | Decameric dimers |
| 10,000 fold excess of PCHPC | Single pentamers |

These effects are absolutely calcium dependent. In the absence of free calcium ions, PCHPC has no effect on molecular assembly of CRP Mass spectrometry analysis provides further precise evidence for calcium-dependent complexes between CRP and PCHPC.

Examination of isolated pure native human CRP in solution in the absence of calcium, with or without PCHPC, reveals the presence predominantly of the expected pentamers, with $M_r$ close to the calculated value for 5 protomers each of $M_r$ 23027 according to the known covalent structure. Small traces of higher $M_r$ species corresponding precisely to decamers are also present. In the presence of both PCHPC and calcium ions, however, the decameric species predominates and has a higher $M_r$ than the decamers seen in pure CRP alone. The difference in $M_r$ between the decamers of CRP alone and those formed with PCHPC and calcium is in the range of 2840-2890, corresponding most closely to 5 PCHPC molecules ($M_r$ 448 each) and 20 calcium ions ($M_r$ 40 each) per pair of CRP pentamers.

Figure 2A:
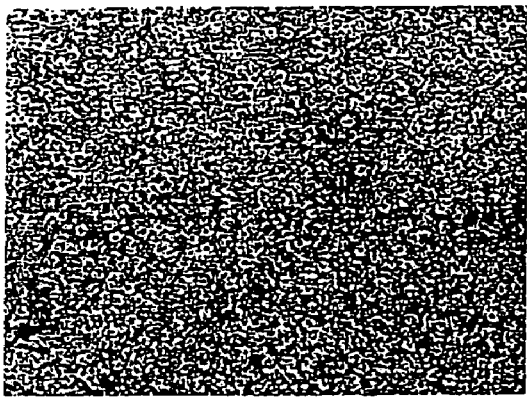
FIG. 2a shows negatively stained electron micrographs of human native pentameric CRP alone.
Figure 2B:
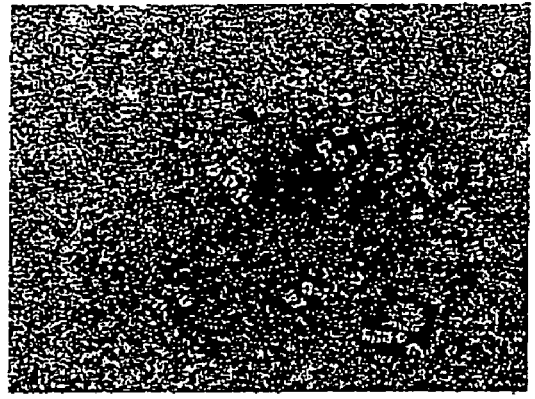
FIG. 2b shows dimers of CRP formed after mixing with PCHPC.
Figure 2C:
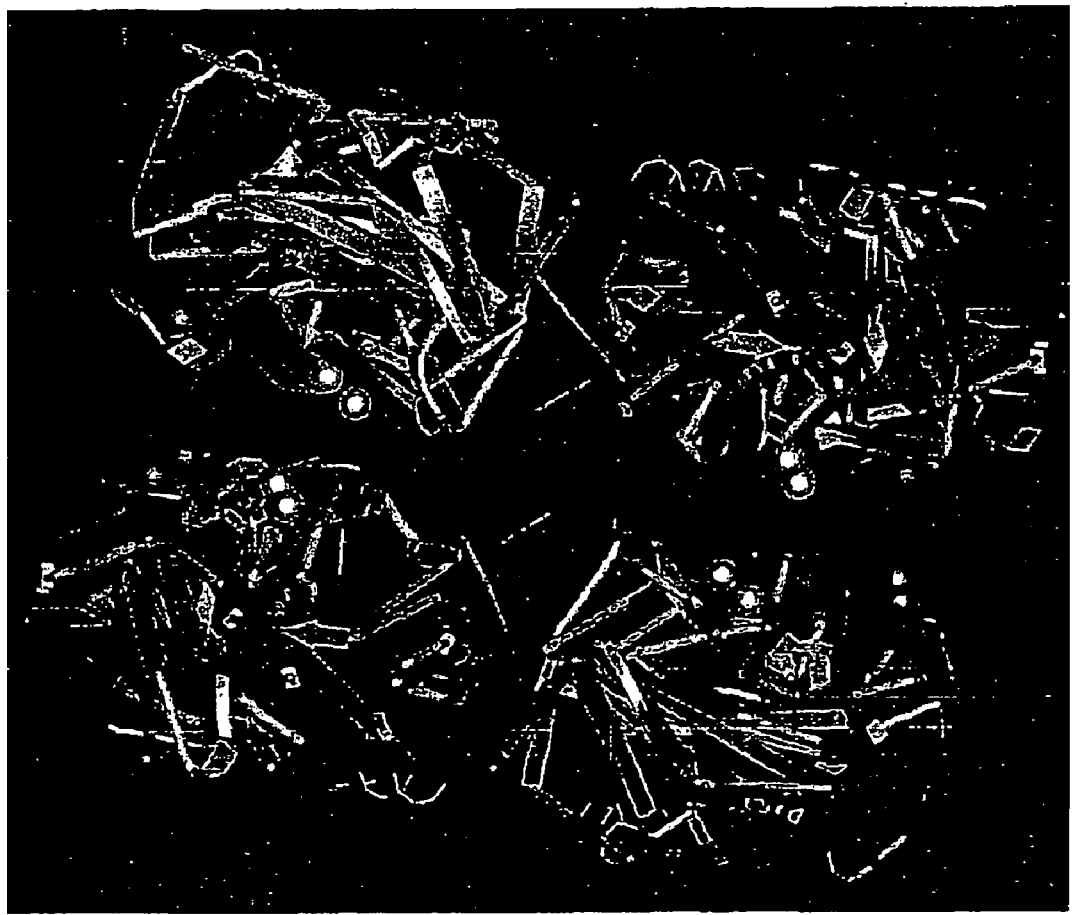
FIG. 2c shows a ribbon representation of the X-ray crystal structure of the CRP—PCHPC complex, showing two pentameric CRP molecules interacting face to face; the pair of calcium atoms in the ligand binding pocket of each protomer are shown as spheres. The structure corresponding to the electron density of the PCHPC molecules is not shown.

The pairing of CRP molecules by PCHPC is also graphically demonstrable by direct electron microscopy as shown in FIG. 2b. Furthermore the structure of the CRP-PCHPC complex solved by X-ray crystallography shows pairs of pentameric CRP molecules interacting face to face (FIG. 2c), exactly as predicted by the design of the PCHPC molecule according to the present invention.

Figure 3:
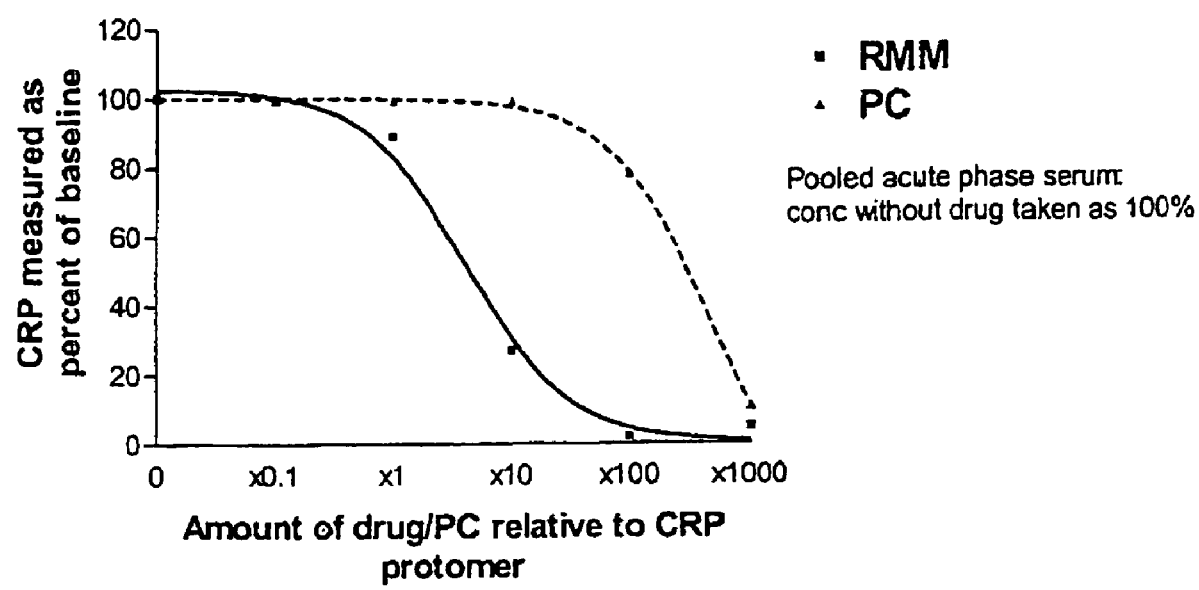
FIG. 3 shows the effect of PCHPC (lot number RMM) on CRP concentration measured by MIRA.

The Roche MIRA automated immunoassay for CRP (64) depends on recognition by a monoclonal antibody of a calcium-dependent epitope on the CRP molecule. The formation by PCHPC of CRP dimers in which the calcium-dependent ligand binding site is occluded, masks this epitope and makes the CRP-PCHPC complex undetectable in the assay (FIG. 3). This provides a convenient method for demonstration of such complexes, generated in vitro or in vivo. This is shown in FIG. 3 in which CRP concentration is measured by MIRA in the presence of PCHPC (lot number RMM) solid line, compared to effect of free phosphocholine, broken line. Identical results were obtained with isolated pure CRP and with CRP in whole acute phase serum.

Figure 4:
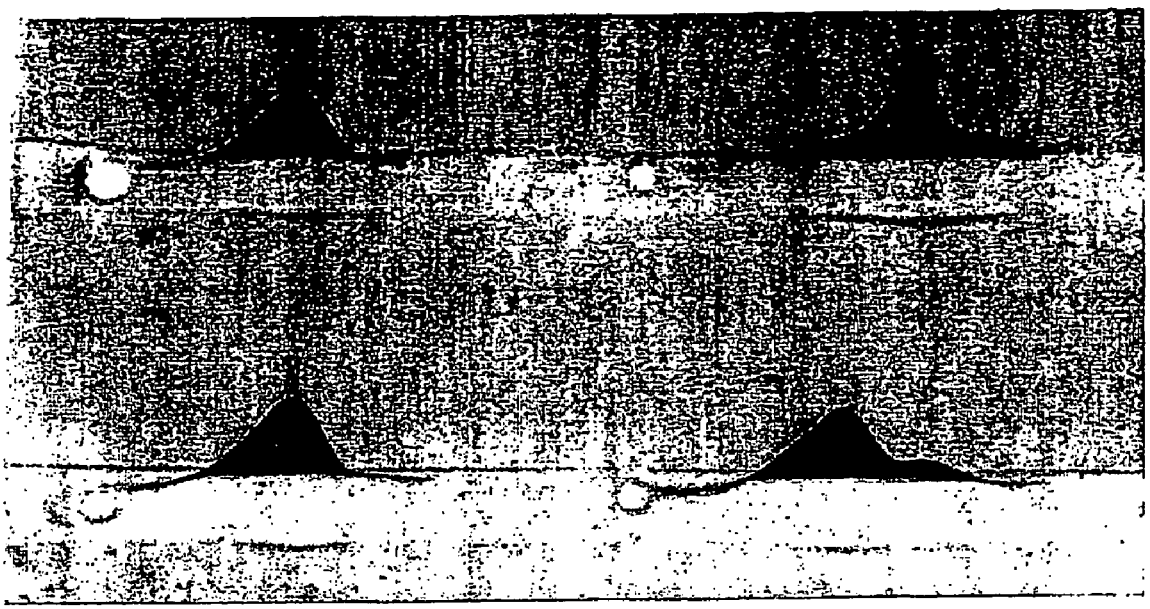
FIG. 4 shows activation of complement component C3 in whole serum shown by 2D immunoelectrophoresis, and its inhibition by PCHPC.

A major mechanism by which the pro-inflammatory, tissue damaging effects of CRP is mediated in vivo, is via activation of the complement system. It is therefore critical that drugs, according to the present invention, that block such adverse effects of CRP should inhibit complement activation by CRP. PCHPC is potent in this respect as shown in FIG. 4. FIG. 4 shows activation of complement component C3 in whole serum shown by 2D immunoelectrophoresis, and its inhibition by PCHPC. Upper left, normal human-serum (NHS) incubated alone at 4° C. showing no C3 activation; upper right, NHS incubated at 37° C. with CRP and CPS showing complete activation of C3; lower left, NHS incubated alone at 37° C. showing no C3 activation; lower right, NHS incubated at 37° C. with CRP and CPS together with PCHPC, showing almost complete inhibition of C3 activation.

Figure 5:
FIG. 5 shows foam cell formation by vascular smooth muscle cells cultured in vitro with low density lipoprotein (LDL) and CRP.
Figure 6:
FIG. 6 shows inhibition of foam cell formation by vascular smooth muscle cells cultured in vitro in the presence of LDL and CRP, together with PCHPC.

It is also critical that drugs, according to the present invention, should block other pathogenetic effects of CRP. The accumulation of LDL within the cytoplasm of macrophages and vascular smooth muscle cells to form foam cells is a characteristic feature of atherosclerotic plaques. When such cells are cultured with LDL in vitro they do not form foam cells unless the cells are stimulated by exposure to pro-inflammatory cytokines or other cell activating agents. However addition of CRP to cells cultured with LDL leads to foam cell formation in the absence of any other stimulating or activating agents (FIG. 5), and if this occurred in vivo it would provide a mechanism by which increased CRP production could be directly pro-atherogenic. FIG. 5 shows foam cell formation by vascular smooth muscle cells cultured in vitro with low density lipoprotein (LDL) and CRP. Ingested and retained intracellular LDL is stained with Oil Red O dye. In the absence of CRP, LDL alone does not accumulate in the cells. Importantly, addition of PCHPC to cultures of smooth muscle cells including both LDL and CRP, effectively inhibits the formation of foam cells (FIG. 6).

Figure 7:
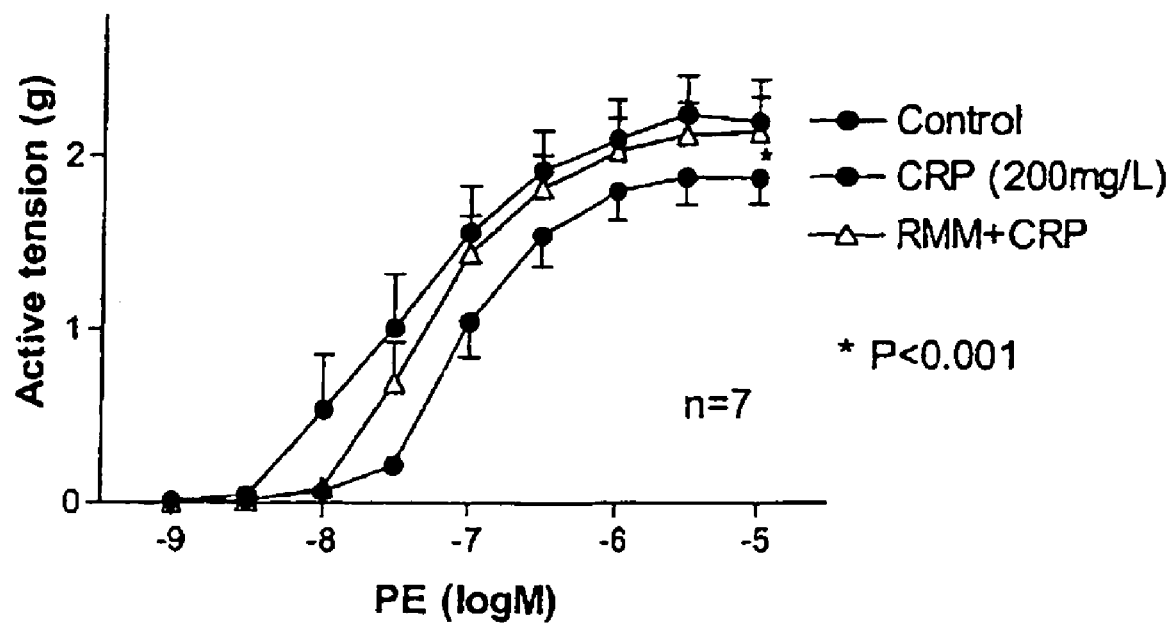
FIG. 7 shows the effect of CRP on vascular response to phenylephrine (PE) and inhibition by PCHPC.

It is generally accepted that endothelial dysfunction, commonly recognised as relative failure of appropriate vascular relaxation and dilatation in vivo, is associated with development and progression of atherosclerosis leading to cardiovascular disease. Reduction of appropriate production of nitric oxide is, in turn, associated with such failure of vascular dilatation and it has been claimed that CRP reduces nitric oxide production in blood vessel walls and endothelial cells in vitro. However our own studies have shown very reproducibly that human CRP actually reduces the vasoconstrictor response of human and rat blood vessels exposed to phenylephrine in vitro, as a result of increased nitric oxide production mediated by up-regulation of eNOS (FIG. 7). It is not clear what pathophysiological significance this effect of CRP may have in relation to atherosclerosis or other pathologies in vivo. However, it is a robust biological action of CRP, and it is therefore a very important proof of principle, according to the present invention, that it is completely abrogated by inclusion of PCHPC in the experiment (FIG. 7).

FIG. 7 shows the effect of CRP on vascular response to phenylephrine (PE) and inhibition by PCHPC. Contraction of the explanted artery in response to PE is significantly reduced by addition of CRP to the culture medium. This is due to upregulation of eNOS by CRP (data not shown here) and correspondingly increased production of NO (data not shown), which is a vascular relaxant. The effect of CRP is completely inhibited by addition of PCHPC (lot number RMM).

Administration in vivo of PCHPC to mice previously injected with human CRP, leads to formation of PCHPC-CRP complexes that are demonstrable in the circulation. Thus there is loss of CRP reactivity in the MIRA assay whilst full reactivity of the CRP is retained in electroimmunoassay for CRP using polyclonal antibodies. The electroimmunoassay is run in the presence of EDTA that chelates calcium and releases CRP from the complexes. Furthermore, after administration of PCHPC to mice injected with human CRP, the CRP in the serum fails to bind ex vivo to phosphoethanolamine immobilised on Sepharose beads. For example, in serum from a mouse given human CRP but no drug, 96% of the CRP at 45 mg/l bound to Sepharose-PE, whereas with serum from a mouse given a single dose of PCHPC as well as CRP, only 17% of 47 mg/l was able to bind to Sepharose-PE.

Figure 8:
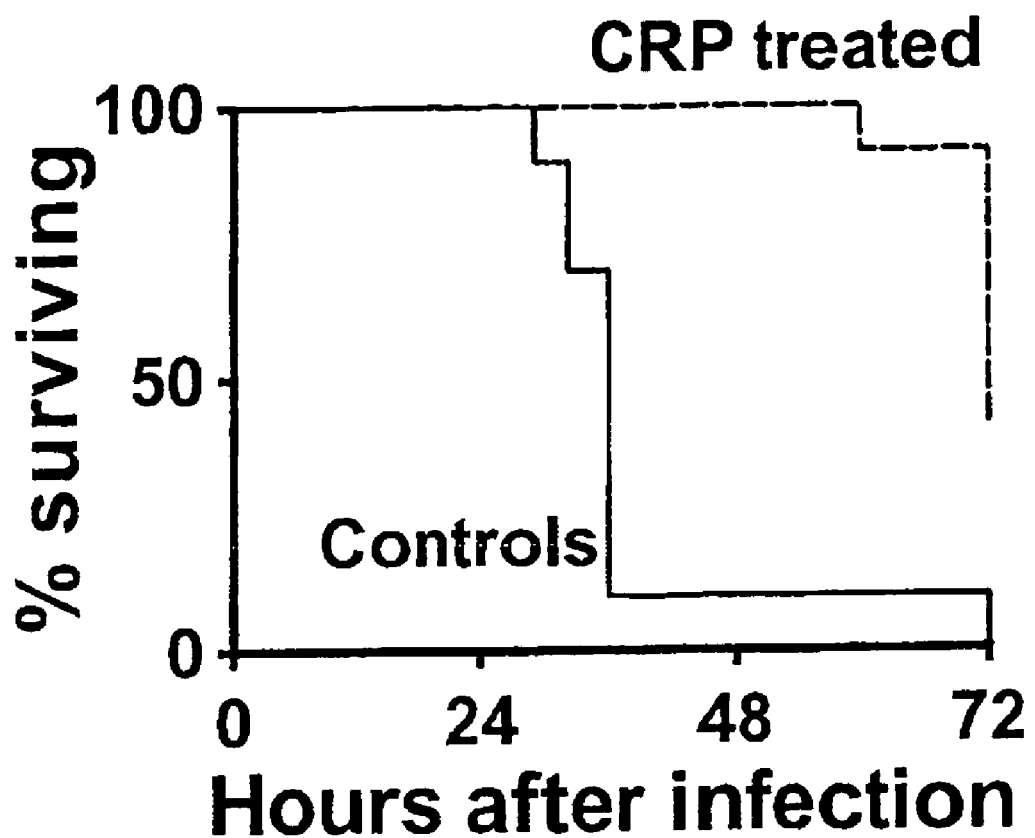
FIG. 8 shows that CRP protects mice against lethal infection with *Streptococcus pneumoniae*.

Clinical efficacy of PCHPC, according to the present invention, requires that PCHPC not only block binding of CRP to its ligands in vivo, but that this also abrogates biological effects of CRP in vivo. It has long been known that administration of human CRP to mice can protect the animals against lethal infection with *Streptococcus pneuinoniae*, and a typical example of such protection is shown in FIG. 8.

Figure 9:
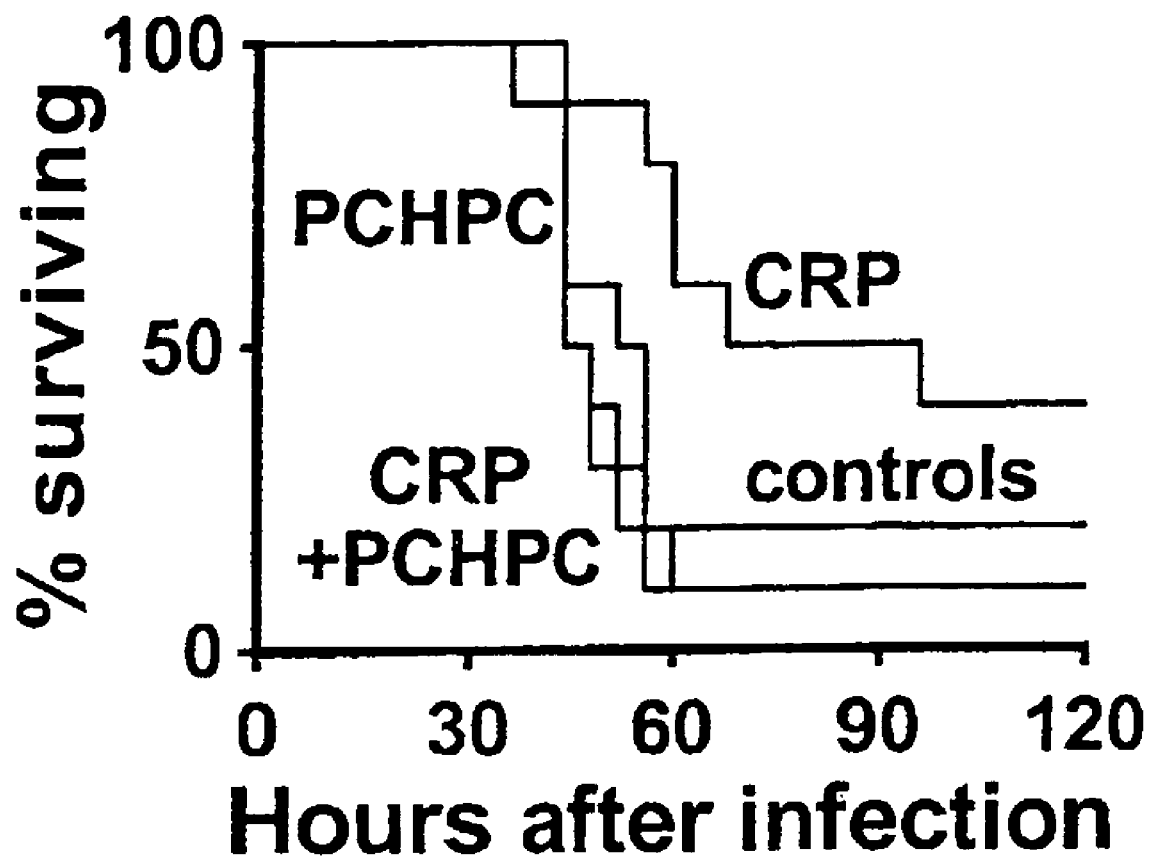
FIG. 9 shows that PCHPC completely abrogates the protective effect of CRP against lethal infection with *Streptococcus pneumoniae* in vivo.

When mice infected with *Streptococcus pneumoniae* and also receiving human CRP are given repeated injections of PCHPC, the CRP mediated protection is completely abrogated, as shown in FIG. 9. These observations clearly show that PCHPC potently abrogates a powerful in vivo biological action of human CRP and is therefore a suitable compound for use according to the present invention.

Figure 10:
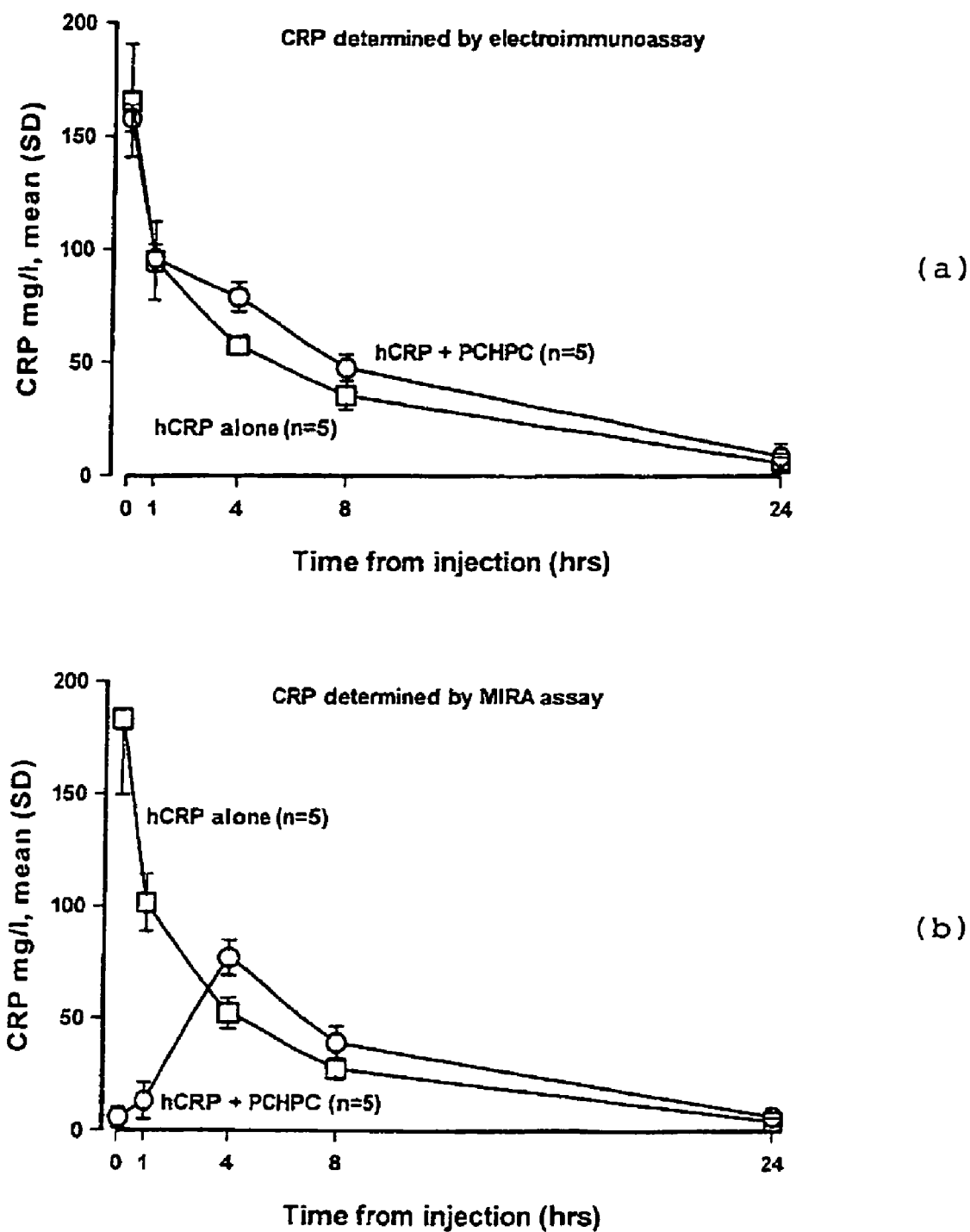
FIG. 10 shows that PCHPC does not affect the clearance of human CRP from the circulation of mice in vivo, shown in FIG. 10(a) by electroimmunoassay, despite initially complexing with the CRP, as shown clearly in FIG. 10(b) below by loss of CRP immunoreactivity in the MIRA assay.

Although PCHPC inhibits complement activation by CRP, and forms complexes with CRP in vitro and in vivo, that block binding of CRP to other ligands in vitro and in vivo, administration of PCHPC in vivo does not affect the rate of clearance of CRP from the circulation, as shown in the upper panel of FIG. 10(a). When the same samples from this experiment are measured in the MIRA assay for CRP (FIG. 10 (b),), the effect of the drug in forming complexes with CRP and thereby abolishing its immunoreactivity in this assay is evident. However, the PCHPC itself is rapidly cleared and after 4 hours the human CRP circulating in the mice becomes fully detectable in the MIRA assay, clearing at the same rate as in untreated control animals.

The failure of PCHPC to affect clearance of human CRP from the plasma of mice, despite formation of drug-CRP complexes, is consistent with published work showing that human CRP is always cleared at a constant fast rate in normal human subjects and in patients with a range of different diseases (31). Also studies in experimental animals similarly show that human CRP is always cleared at the same rate, regardless of the presence even of avid macromolecular ligands, such as CPS (65). This phenomenon contrasts sharply with the behaviour in vivo of the closely related molecule, serum amyloid P component (SAP), the other member of the human pentraxin protein family. SAP shares with CRP the homopentameric structure consisting of 5 identical protomers non-covalently associated in a disc like configuration, with a single calcium-dependent ligand binding site on one face of each subunit. However, when the palindromic molecule, (R)-1-[6-[(R)-2-Carboxy-pyrrolidin-1-yl]-6-oxo-hexanoyl]pyrrolidine-2-carboxylic acid (abbreviated as CPHPC), which is recognised and bound by SAP, forms complexes with SAP comprising pairs of SAP molecules cross linked by CPHPC, these complexes are very rapidly cleared from the circulation in vivo (66,67). The handling of aggregated human SAP in vivo may thus differ markedly from that of aggregated CRP. Alternatively, the complexes between CRP and PCHPC may be less stable than those formed by SAP and CPHPC. The affinity of binding, measured by isothermal calorimetry is 10 nM for SAP and CPHPC compared to 400 nM for CRP and PCHPC. Mouse SAP binds less avidly to all ligands than does human SAP, and administration of CPHPC to mice does not accelerate clearance of mouse SAP in vivo, whereas it dramatically clears human SAP expressed in human SAP transgenic mice (67). Thus compounds that are both bound by CRP with higher affinity and that cross-link it in more avid stable complexes, may cause accelerated clearance from the plasma in vivo.

Compounds that, like PCHPC, not only inhibit ligand binding by CRP but also promote accelerated clearance of CRP, thereby rendering it unavailable for production of adverse, pathogenetic, effects are desirable according to the present invention. Such compounds are characterised by high affinity binding by CRP, by virtue of accessory interactions with the protein, in addition to recognition of the phosphocholine head group in the calcium-dependent binding pocket. For example, there is a small hydrophobic cleft adjacent to phosphocholine binding site, that can accommodate a methyl or other small hydrophobic group, and attachment of a suitably-placed group at each end of the PCHPC molecule markedly increases the affinity of binding by CRP (68). Binding affinity and the avidity of formation of drug-CRP complexes are also increased by modification of the aliphatic linker between the two phosphocholine head groups, for example, altering the length of the chain, including double bonds to rigidify it in optimal conformations, inclusion of aromatic groups and of side chains that can generate drug protein interactions additional to the calcium-dependent binding of phosphocholine.

More specifically, an important component of the calcium-dependent binding of phosphocholine in the ligand binding pocket of CRP is the electrostatic interaction between the quaternary ammonium of choline and residue Glu81. This charge interaction is maintained in bisphosphoethanolamine compounds with longer chain lengths than the 6 carbons in PCHPC, for example with 7 or more carbon atoms, and such compounds of the general formula shown below are desirable according to the present invention.

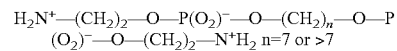

$$H_2N^+ \text{---} (CH_2)_2 \text{---} O \text{---} P(O_2)^- \text{---} O \text{---} (CH_2)_n \text{---} O \text{---} P(O_2)^- \text{---} O \text{---} (CH_2)_2 \text{---} N^+H_2 \quad n=7 \text{ or } >7$$

Other phosphate containing head groups that can be made palindromic according to the present invention are shown below. Compounds 1, 5 and 6 provide a ring stacking with Trp66 in the CRP ligand binding pocket, and thereby increasing binding affinity, whilst maintaining the calcium coordination. Compounds 5 and 6 also enable the formation of hydrogen bonds between ring nitrogens and polar groups that interact with the quaternary nitrogen of phosphocholine in its complex with CRP (68).

Another variation that increases affinity of binding is replacement with an amino group of one of the hydrogen atoms on one of the methyl groups on each of the quaternary nitrogens of the bisphosphocholine structure. This enables hydrogen bonding to residues Ser68 and/or Ser74 that are close to the choline head group and thereby produces higher affinity binding that is desirable according to the present invention. The head group with this structure is shown at 2 in the structural formulae below. Compounds 3 and 8 have the same desirable substitution in the choline group and also include five or six membered ring sidegroups, respectively, that pack into the ligand binding pocket of CRP and form additional hydrogen bonds to the critical polar residue Thr76 that constitutes one of the pocket walls, as explained further below. Compound 7 advantageously provides a hydroxy-proline like ring that can hydrogen bond to Thr76, the positively charged amino group is smaller than the choline quaternary nitrogen and enables the whole head group to fit more snugly into the pocket. This yields high affinity binding that is desirable according to the present invention.

Compound 4 is a D-proline derivative that provides a carboxylate instead of a phosphate acidic group, and has an extended amino group that reaches over to the glutamate residue that normally binds the positive N of choline. The carbon atom preceding the carboxyl, arrowed in the structural formulae, is the attachment site for the linker. For all the other head groups shown the linker is attached via the hydroxyl group of the phosphate, as in PCHPC.

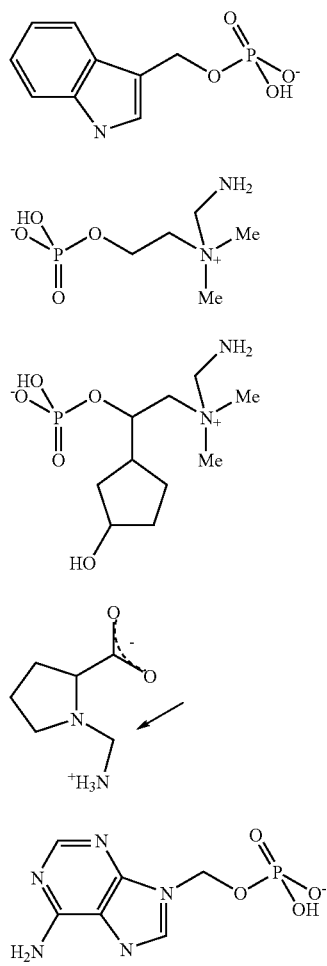

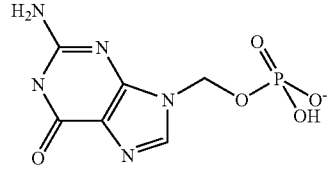

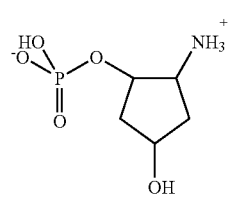

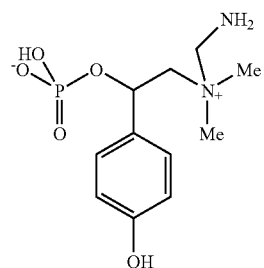

The calcium-dependent ligand binding pocket for phosphocholine in CRP (68) is slightly larger than the calcium-dependent ligand binding pocket of SAP that binds a D-proline residue (67). The CRP pocket also has a polar side by virtue of the replacement of residues Tyr74, Tyr64 and Leu62 that line the SAP pocket, and bind 3 of the 4 proline carbons, by CRP residue Thr76. In order to fill the CRP pocket it is necessary to overcome its closeness to the calcium atoms which critically ligate the phosphate or other acidic moiety. In phosphate esters the extra O atom in the chain displaces the head group, and branch substituents added to the linker, from the pocket. Replacement of the O ester atom by a 2 carbon fragment enables a polar branch moiety at the end of the linker to enter the pocket and hydrogen bond to Thr74, thereby creating higher affinity binding. Palindromic compounds of this type are therefore desirable according to the present invention.

With regard to the linker chain, the 6 carbon length in PCHPC is optimised on the position of the calcium-dependent ligand binding sites on the CRP protomers, that are tipped away from the five fold axis of the intact pentamer (68), but a chain comprising 5 or 7 methylene groups is also desirable according to the present invention. With 5 methylenes more pentamer-pentamer contacts are permitted, and these desirably increase the avidity of binding. With 7 methylene groups the linker can buckle to optimise positioning of the phosphocholine head group in the ligand binding pocket, and thereby desirably increase binding affinity. Inclusion in the linker chain of double bonds, to reduce flexibility, desirably increases binding avidity and also improves pharmacological properties. An example of such a compound and its synthesis are shown below.

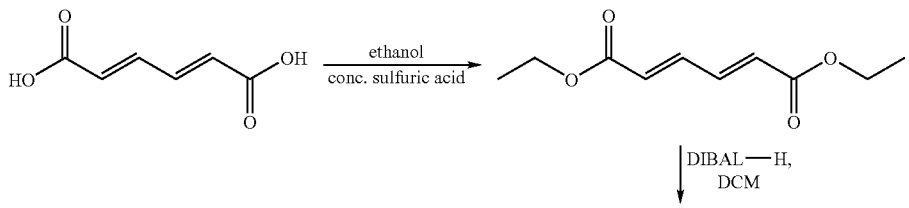

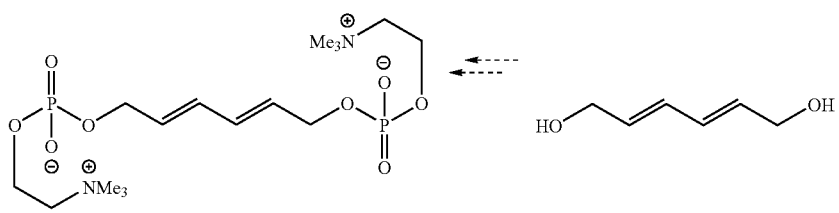

Diethyl-trans-trans-muconic acid. To a solution of trans-trans-muconic acid (2.0 g, 9.71 mmol) in absolute ethanol (10 mL) was added concentrated sulfuric acid (1 mL) and the resulting mixture heated at reflux for 16 h. The resulting solution was diluted with saturated sodium hydrogen carbonate until just basic. The solid that was formed was filtered and recrystallised from ethanol:water (1:1) to yield a white crystalline solid (1.8 g, 64%). 1H NMR (400 MHz, CDCl$_3$) 7.29 (2H, m, =CH), 6.19 (2H, m, =CH), 4.22 (2H, q, J 12, CH$_2$), 1.31 (3H, t, J 12, CH$_3$). trans-trans-Muconol. To a stirring solution of diethyl-trans-trans-muconic acid (1.67 g, 8.4 mmol) in anhydrous dichloromethane (60 mL) was added an ethereal solution of dibutylaluminium hydride (1.0 M, 33.6 mL, 4 eq) via a syringe pump over a period of 30 mins. After addition was complete, the yellow solution was allowed to warm to 20° C. and stirred for 8 h. After this time, the reaction was quenched with excess methanol (250 mL) to destroy any unreacted dibutylaluminium hydride and the mixture allowed to stir for 1 h. After this time, the resulting suspension was filtered, the filtrate kept separate and the residue ground in a mortar with more methanol which was again filtered through celite and combined with the initial filtrate. The combined organic layers were dried (MgSO$_4$), filtered and evaporated to give a yellow oil which was purified by flash column chromatography (Ethyl acetate:petroleum ether, 7:3). The phosphocholine ligand head groups were then attached to the terminal hydroxyl groups of the trans-trans-muconol, precisely as described above for the synthesis of PCHPC.

Another linker that is desirable according to the present invention includes aryl components that promote higher affinity binding of the phosphocholine head groups by CRP and provide for enhanced drug-protein interactions leading to more avid and effective complex formation as well as improved pharmacological properties. An example of the synthetic pathway for such a compound is shown below, in which creation of the linker as a suitable alcohol is followed by the attachment of the phosphocholine head groups as described above for PCHPC.

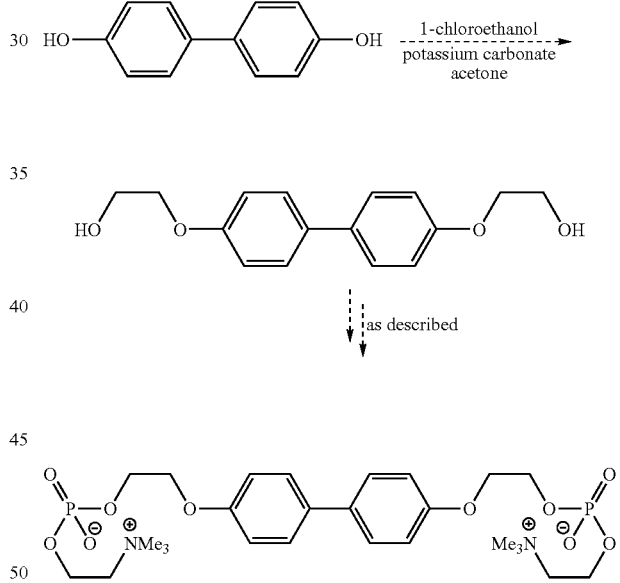

Substituents on the linear linker chain are also desirable according to the present invention by virtue of their capacity to enable secondary interactions with the CRP molecule and thereby increase affinity and avidity of binding. The binder may have a hydrophobic substituent at a position proximal to each ligand for interaction with the ligand linding site present on CRP. An example is shown below in which a methyl side chain on the linker carbon atom proximal to each phosphocholine head group is suitably placed to form a hydrophobic interaction with a small hydrophobic pocket in the CRP structure adjacent to the calcium-dependent ligand binding site (68). This substantially increases the affinity with which the compound is bound by CRP. Synthesis of this compound is shown here.

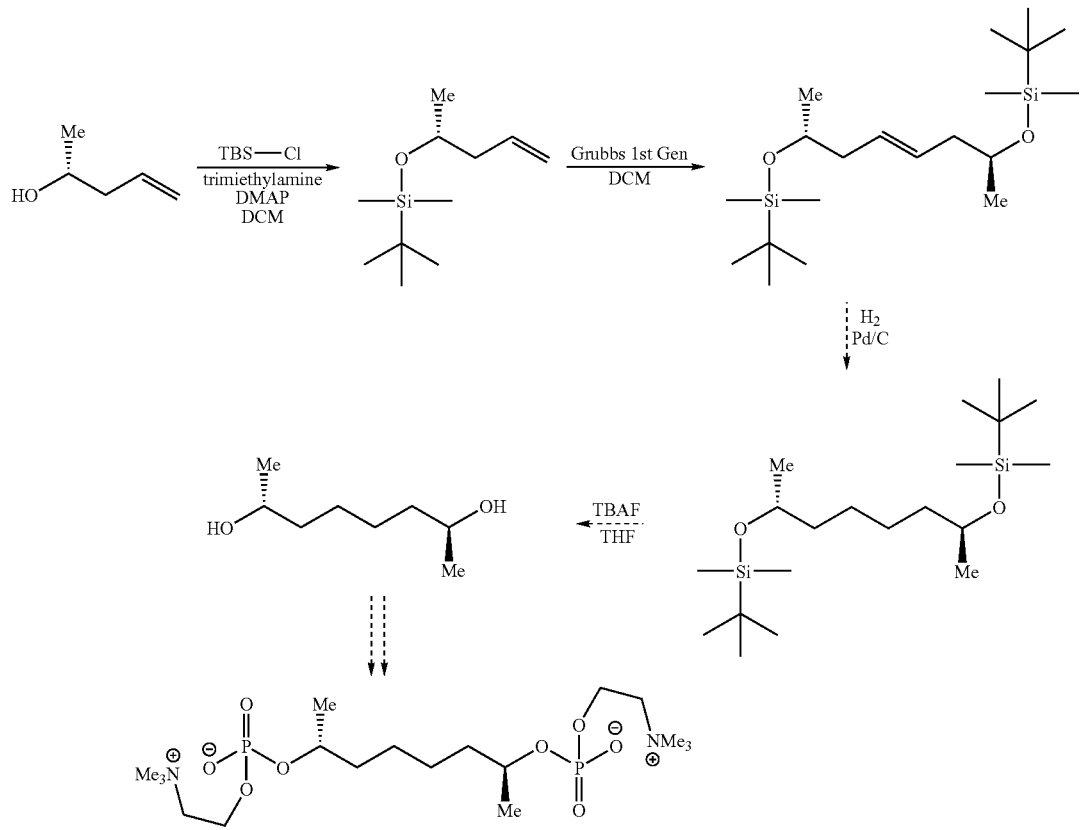

(R)—O-tert-butlydimethylsilyl-penten-2-ol. A solution of (R)-(-)-penten-2-ol (2 mL, 19.4 mmol), triethylamine (5.4 mL, 38.9 mmol) and DMAP (0.237 g, 1.94 mmol) in dichloromethane (25 mL) was cooled to 0° C., followed by the addition of a solution of TBDMS chloride (3.81 g, 25.3 mmol). The mixture was allowed to warm to 20° C. and stirred for 17 h, whereupon saturated ammonium chloride was added (100 mL) and the aqueous layer extracted with ethyl acetate (2×100 mL). The combined organic phases were dried (MgSO$_4$), filtered and evaporated to give a clear oil which was purified by flash column chromatography (petroleum ether 40-60, 100%) to give a clear oil (3 g, 77%).

O,O-2,7-di-(tert-butlydimethylsilyl)-oct-4-ene. To a solution of (R)-O-tert-butlydimethylsilyl-penten-2-ol (2 g, 10 mmol) in DCM (60 mL) was added Grubb's 1$^{st}$ generation catalyst (0.206 g, 25 mol %) and the resulting mixture heated at reflux for 16 h. After this time the reaction was diluted with water (100 mL) and the aqueous layer extracted with ethyl acetate (2×100 mL). The combined organic layers were dried (MgSO$_4$), filtered and evaporated to give a black oil which was purified by flash column chromatography (hexane, 100%) to give a clear oil. Subsequent: reduction and hydrolysis yield the desired linker as an alcohol suitable for attachment of the phosphocholine head groups as described for PCHPC.

Multimeric drug compounds with multiple phosphocholine or other head groups bound by CRP, appropriately spaced to interact with more than one protomer on each pair of CRP molecules in the drug cross-linked diner, produce very avid and stable drug-CRP complexes, and are desirable according to the present invention. In particular, compounds with ligand head groups in an array appropriately spaced to be bound by each of the five ligand binding pockets on the planar binding (B) face of the CRP molecule are desirable for the greatly increased avidity engendered by such multiple interactions.

Another approach to inhibition and clearance of CRP according to the present invention, is to use a heterobifunctional compound with phosphocholine, or any one of the various different head groups described above that are recognised by CRP, as one head group and D-proline, recognised by SAP, as the other head group. A typical example of this type of structure, shown below,

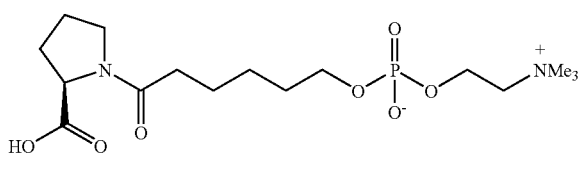

produces mixed complexes comprising one CRP and one SAP molecule cross-linked by the drug. Binding of the phosphocholine or related head group by CRP inhibits the capacity of CRP to interact with other ligands, occlusion of the B face of the CRP molecule enhances this inhibition, and, importantly, complexing and aggregation with SAP creates a complex that is recognised as abnormal in vivo and is promptly cleared from the circulation. Such clearance further enhances the potency of the drug, according to the present invention, in abrogating the adverse, pathogenetic, effects of CRP and thereby in ameliorating disease.

As described above with respect to PCHPC, occlusion of the B face of the CRP molecule, that bears the epitopes recognised by one of the monoclonal anti-CRP antibodies in the MIRA assay for CRP, reduces the amount of CRP that is detected in this assay. Similarly, the heterobifunctional ligand compound shown here, D-Pro-hexanoyl-phosphocholine (DPHPC), that is bound by CRP via the phosphocholine group, slightly reduces apparent CRP concentration in the MIRA assay when added to isolated pure CRP, presumably by simple steric hindrance. However in the presence of pure SAP, DPHPC reduces the MIRA CRP concentration dramatically and in a dose dependent fashion. In a typical experiment with CRP at 100 mg/l, approximating to 4 μM, and DPHPC at 4 mM, the MIRA value was reduced by 91%, but with DPHPC at 400 μM there was no effect. When SAP was also present at 100 mg/l, approximating to 4 μM, the MIRA CRP concentration was reduced by 99% with 4 mM DPHPC, by 89% with 2 mM DPHPC, and by 58% with 400 μM DPHPC. This powerful effect is also dependent on the SAP concentration. For example, in another typical experiment with approximately 4 μM CRP and 1 mM DPHPC, MIRA CRP concentration was reduced by 62%. However, with SAP also present at about 4 μM, the MIRA CRP value was reduced by 85%; with SAP at 2 μM the reduction was 73%, and with SAP at either 800 nM or 400 nM it was 61%, that is the same as without any SAP. Importantly, DPHPC has the same effect of producing mixed CRP-SAP complexes, in which the CRP is not detected in the MIRA assays, when the drug is added to whole serum containing equimolar amounts of CRP and SAP. Thus in whole serum containing approximately 4 μM CRP, addition of 4 mM DPHPC reduced by 19% the concentration of CRP detectable in the MIRA assay. In the absence of DPHPC, addition of SAP to a final concentration of about 4 μM had no effect and all the CRP present was detected by MIRA. However when DPHPC was added at 4 mM to serum containing SAP and CRP both at around 4 μM, the MIRA CRP value was reduced by 44%. With 2 μM SAP the reduction fell to 29%, and at lower SAP concentrations there was no enhancement of the effect of DPHPC alone.

Multimeric compounds capable of being bound by both CRP and SAP provide for higher avidity interactions and are therefore more stable mixed complexes of CRP and SAP molecules. This inhibits CRP binding more effectively and also more efficiently promotes clearance of CRP. Such compounds are desirable according to the present invention. A typical example is shown below in which the ligand head groups are appropriately spaced to interact with each of the five ligand binding pockets on the B face of CRP and SAP respectively. The D-proline head groups, recognised by SAP, are on one face of the compound while the phosphocholine head groups (indicated by R in the diagram), recognised by CRP, are on the opposite face.

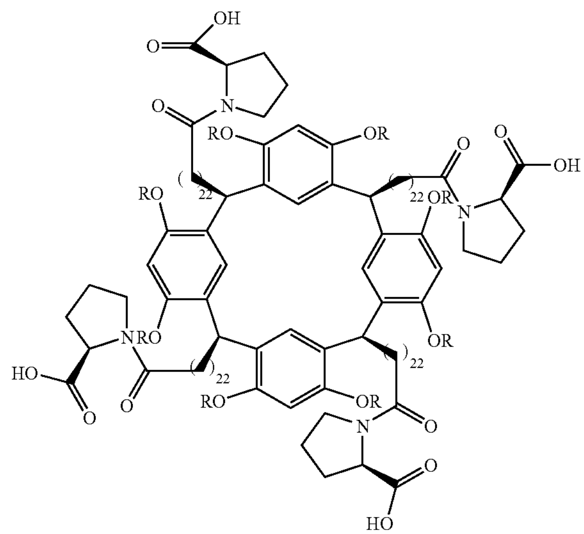

The first stage of the synthesis of this compound is shown here, comprising formation of the ring, above, and attachment of the phosphocholine head groups, below.

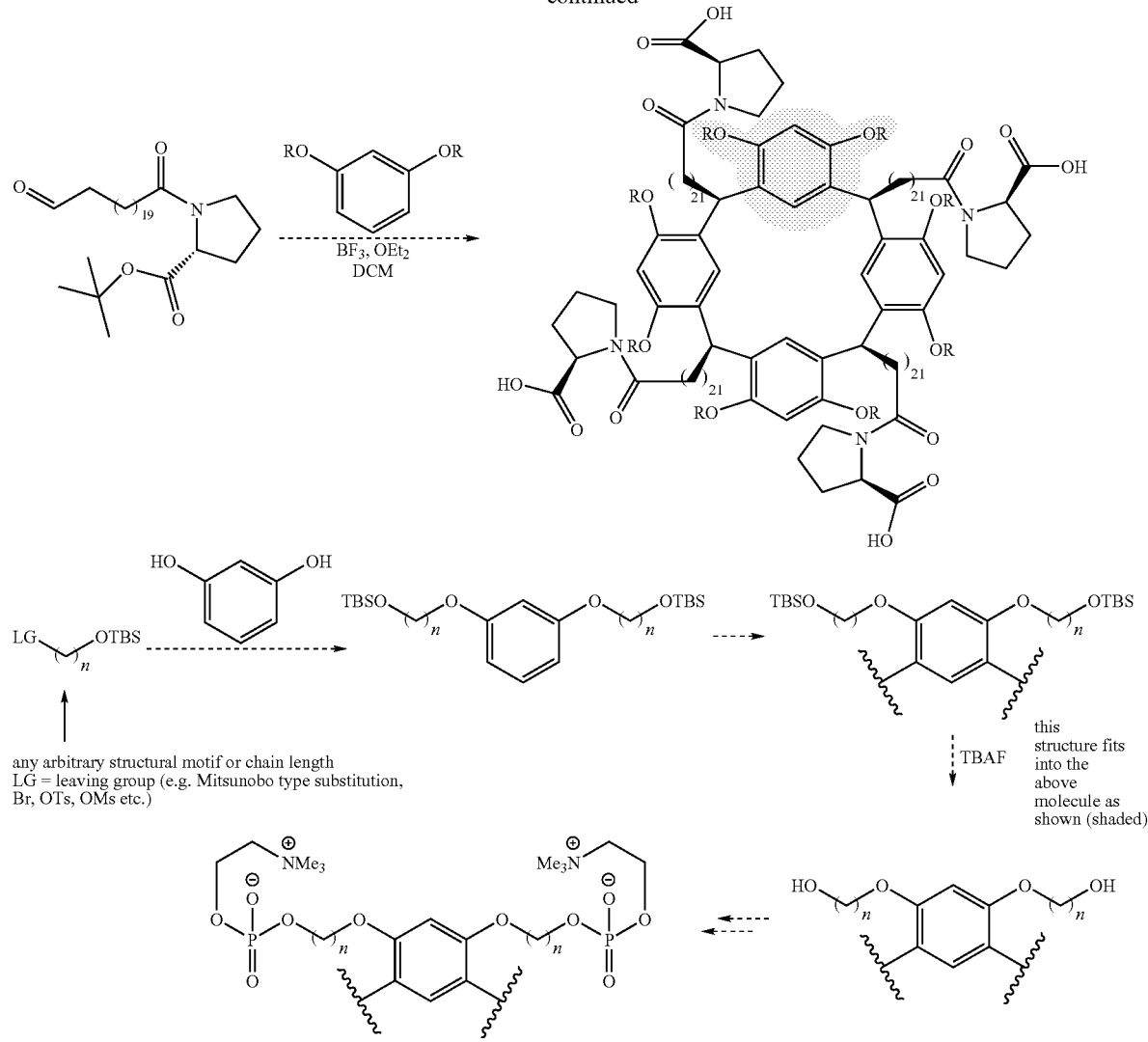

REFERENCES

1. Pepys, M. B. and Baltz, M. L. (1983) Acute phase proteins with special reference to C-reactive protein and related proteins (pentaxins) and serum amyloid A protein. *Adv. Immunol.*, 34: 141-212.
2. Pepys, M. B. (1996) The acute phase response and C-reactive protein. *In: Oxford Textbook of Medicine, Third Ed.*, Vol. 2 (Weatherall, D. J., Ledingham, J. G. G. and Warrell, D. A., eds.), Oxford University Press, Oxford, pp. 1527-1533.
3. Volanakis, J. E. and Kaplan, M. H. (1971) Specificity of C-reactive protein for choline phosphate residues of pneumococcal C-polysaccharide. *Proc. Soc. Exp. Biol. Med.*, 136: 612-614.
4. de Beer, F. C., Soutar, A. K., Baltz, M. L., Trayner, I., Feinstein, A. and Pepys, M. B. (1982) Low density and very low density lipoproteins are selectively bound by aggregated C-reactive protein. *J. Exp. Med.*, 156: 230-242.
5. Pepys, M. B., Rowe, I. F. and Baltz, M. L. (1985) C-reactive protein: binding to lipids and lipoproteins. *Int. Rev. Exp. Pathol.*, 27: 83-111.
6. Narkates, A. J. and Volanakis, J. E. (1982) C-reactive protein binding specificities: artificial and natural phospholipid bilayers. *Ann. N.Y. Acad. Sci.*, 389: 172-182.
7. Volanakis, J. E. and Wirtz, K. W. A. (1979) Interaction of C-reactive protein with artificial phosphatidylcholine bilayers. *Nature*, 281: 155-157.
8. Du Clos, T. W. (1989) C-reactive protein reacts with the U1 small nuclear ribonucleoprotein. *J. Immunol.*, 143: 2553-2559.
9. Pepys, M. B., Booth, S. E., Tennent, G. A., Butler, P. J. G. and Williams, D. G. (1994) Binding of pentraxins to different nuclear structures: C-reactive protein binds to small nuclear ribonucleoprotein particles, serum amyloid P component binds to chromatin and nucleoli. *Clin. Exp. Immunol.*, 97: 152-157.
10. Kindmark, C.-O. (1972) In vitro binding of human C-reactive protein by some pathogenic bacteria and zymosan. *Clin. Exp. Immunol.*, 11: 283-289.
11. Fletcher, T. C., White, A. and Baldo, B. A. (1980) Isolation of a phosphorylcholine-containing component from the 11. [continued] turbot tapeworm, *Bothriocephalus scorpii* (Muller) and its reaction with C-reactive protein. *Parasite Immunol.*, 2: 237-248.

12. de Beaufort, A. J., Langermans, J. A. M., Matze-van der Lans, A. M., Hiemstra, P. S., Vossen, J. M. and Van Furth, R. (1997) Difference in binding of killed and live *Streptococcus pneumoniae* serotypes by C-reactive protein. *Scand. J. Immunol.*, 46: 597-600.

13. Weiser, J. N., Pan, N., McGowan, K. L., Musher, D., Martin, A. and Richards, J. (1998) Phosphorylcholine on the lipopolysaccharide of *Haemophilus influenzae* contributes to persistence in the respiratory tract and sensitivity to serum killing mediated by C-reactive protein. *J. Exp. Med.*, 187: 631-640.

14. Culley, F. J., Bodman-Smith, K. B., Ferguson, M. A. J., Nikolaev, A. V., Shantilal, N. and Raynes, J. G. (2000) C-reactive protein binds to phosphorylated carbohydrates. *Glycobiology*, 10: 59-65.

15. Lysenko, E., Richards, J. C., Cox, A. D., Stewart, A., Martin, A., Kapoor, M. and Weiser, J. N. (2000) The position of phosphorylcholine on the lipopolysaccharide of *Haemophilus influenzae* affects binding and sensitivity to C-reactive protein-mediated killing. *Mol. Microbiol.*, 35: 234-245.

16. Kaplan, M. H. and Volanakis, J. E. (1974) Interaction of C-reactive protein complexes with the complement system. I. Consumption of human complement associated with the reaction of C-reactive protein with pneumococcal C-polysaccharide and with the choline phosphatides, lecithin and sphingomyelin. *J. Immunol.*, 112: 2135-2147.

17. Volanakis, J. E. and Kaplan, M. H. (1974) Interaction of C-reactive protein complexes with the complement system. II. Consumption of guinea-pig complement by CRP complexes: requirement for human Clq. *J. Immunol.*, 113: 9-17.

18. Claus, D. R., Siegel, J., Petras, K., Osmand, A. P. and Gewurz, H. (1977) Interactions of C-reactive protein with the first component of human complement. *J. Immunol.*, 119: 187-192.

19. Volanakis, J. E. (1982) Complement activation by C-reactive protein complexes. *Ann. N.Y. Acad. Sci.*, 389: 235-250.

20. Mortensen, R. F., Osmand, A. P., Lint, T. F. and Gewurz, H. (1976) Interaction of C-reactive protein with lymphocytes and monocytes: complement-dependent adherence and phagocytosis. *J. Immunol.*, 117: 774-781.

21. Nakayama, S., Mold, C., Gewurz, H. and Du Clos, T. W. (1982) Opsonic properties of C-reactive protein in vivo. *J. Immunol.*, 128: 2435-2438.

22. Osmand, A. P., Mortensen, R. F., Siegel, J. and Gewurz, H. (1975) Interactions of C-reactive protein with the complement system. III. Complement-dependent passive hemolysis initiated by CRP. *J. Exp. Med.*, 142: 1065-1077.

23. Finland, M. and Dowling, H. F. (1935) Cutaneous reactions and antibody response to intracutaneous injections of pneumococcus polysaccharides. *J. Immunol.*, 29: 285-299.

24. Kushner, I. and Kaplan, M. H. (1961) Studies of acute phase protein. I. An immunohistochemical method for the localization of Cx-reactive protein in rabbits. Association with necrosis in local inflammatory lesions. *J. Exp. Med.*, 114: 961-973.

25. Kushner, I., Rakita, L. and Kaplan, M. H. (1963) Studies of acute phase protein. II. Localization of Cx-reactive protein in heart in induced myocardial infarction in rabbits. *J. Clin. Invest.*, 42: 286-292.

26. Gitlin, J. D., Gitlin, J. I. and Gitlin, D. (1977)-Lo-calisation of C-reactive protein in synovium of patients with rheumatoid arthritis. *Arthritis Rheum.*, 20: 1491-1499.

27. Du Clos, T. W., Mold, C., Paterson, P. Y., Alroy, J. and Gewurz, H. (1981) Localization of C-reactive protein in inflammatory lesions of experimental allergic encephalomyelitis. *Clin. Exp. Immunol.*, 43: 565-573.

28. Lagrand, W. K., Niessen, H. W. M., Wolbink, G.-J., Jaspars, L. H., Visser, C. A., Verheugt, F. W. A., Meijer, C. J. L. M. and Hack, C. E. (1997) C-reactive protein colocalizes with complement in human hearts during acute myocardial infarction. *Circulation*, 95: 97-103.

29. Torzewski, J., Torzewski, M., Bowyer, D. E., Fröhlich, M., Koenig, W., Waltenberger, J., Fitzsimmons, C. and Hombach, V. (1998) C-reactive protein frequently colocalizes with the terminal complement complex in the intima of early atherosclerotic lesions of human coronary arteries. *Arterioscler. Thromb. Vasc. Biol.*, 18: 1386-1392.

30. Wolbink, G.-J., Bossink, A. W. J., Groeneveld, A. B. J., de Groot, M. C. M., Thijs, L. G. and Hack, C. E. (1998) Complement activation in patients with sepsis is in part mediated by C-reactive protein. *J. Infect. Dis.*, 177: 81-87.

31. Vigushin, D. M., Pepys, M. B. and Hawkins, P. N. (1993) Metabolic and scintigraphic studies of radioiodinated human C-reactive protein in health and disease. *J. Clin. Invest.*, 91: 1351-1357.

32. Kew, R. R., Hyers, T. M. and Webster, R. O. (1990) Human C-reactive protein inhibits neutrophil chemotaxis in vitro: possible implications for the adult respiratory distress syndrome. *J. Lab. Clin. Med.*, 115: 339-345.

33. Heuertz, R. M., Xia, D., Samols, D. and Webster, R. O. (1992) Transgenic mice expressing plasma rabbit C-reactive protein exhibit diminished vascular permeability and neutrophil infiltration in C5a-induced alveolitis. *FASEB J.*, 6: 1064 (abstract).

34. Mold, C. and Gewurz, H. (1980) Activation of the alternative pathway by liposomes: inhibitory effect of C-reactive protein. *Fed. Proc.*, 39: 702.

35. Mold, C. and Gewurz, H. (1981) Inhibitory effect of C-reactive protein on alternative C pathway activation by liposomes and *Streptococcus pneumoniae*. *J. Immunol.*, 127: 2089-2092.

36. Gershov, D., Kim, S., Brot, N. and Elkon, K. B. (2000) C-reactive protein binds to apoptotic cells, protects the cells from assembly of the terminal complement components, and sustains an antiinflammatory innate immune response: implications for systemic autoimmunity. *J. Exp. Med.*, 192: 1353-1363.

37. Griselli, M., Herbert, J., Hutchinson, W. L., Taylor, K. M., Sohail, M., Krausz, T. and Pepys, M. B. (1999) C-reactive protein and complement are important mediators of tissue damage in acute myocardial infarction. *J. Exp. Med.*, 190: 1733-1739.

38. Shine, B., de Beer, F. C. and Pepys, M. B. (1981) Solid phase radioimmunoassays for C-reactive protein. *Clin. Chim. Acta*, 117: 13-23.

39. Hutchinson, W. L., Koenig, W., Fröhlich, M., Sund, M., Lowe, G. D. O. and Pepys, M. B. (2000) Immunoradiometric assay of circulating C-reactive protein: age-related values in the adult general population. *Clin. Chem.*, 46: 934-938.

40. Liuzzo, G., Biasucci, L. M., Gallimore, J. R., Grillo, R. L., Rebuzzi, A. G., Pepys, M. B. and Maseri, A. (1994) The prognostic value of C-reactive protein and serum amyloid A protein in severe unstable angina. *N. Engl. J. Med.*, 331: 417-424.

41. Kuller, L. H., Tracy, R. P., Shaten, J. and Meilahn, E. N. (1996) Relation of C-reactive protein and coronary heart-disease in the MRFIT nested case control study. *Am. J. Epidemiol.,* 144: 537-547.
42. Haverkate, F., Thompson, S. G., Pyke, S. D. M., Gallimore, J. R. and Pepys, M. B. (1997) Production of C-reactive protein and risk of coronary events in stable and unstable angina. *Lancet,* 349: 462-466.
43. Ridker, P. M., Cushman, M., Stampfer, M. J., Tracy, R. P. and Hennekens, C. H. (1997) Inflammation, aspirin, and the risk of cardiovascular disease in apparently healthy men. *N. Engl. J. Med.,* 336: 973-979.
44. Ridker, P. M., Cushman, M., Stampfer, M. J., Tracy, R. P. and Hennekens, C. H. (1998) Plasma concentration of C-reactive protein and risk of developing peripheral vascular disease. *Circulation,* 97: 425-428.
45. Ridker, P. M., Buring, J. E., Shih, J., Matias, M. and Hennekens, C. H. (1998) Prospective study of C-reactive protein and the risk of future cardiovascular events among apparently healthy women. *Circulation,* 98: 731-733.
46. Ridker, P. M. (1998) C-reactive protein and risks of future myocardial infarction and thombotic stroke. *Eur. Heart J.,* 19: 1-3.
47. Danesh, J., Collins, R., Appleby, P. and Peto, R. (1998) Association of fibrinogen, C-reactive protein, albumin, or leukocyte count with coronary heart disease. *J. Am. Coll. Cardiol.,* 279: 1477-1482.
48. Koenig, W., Sund, M., Fröhlich, M., Fischer, H.-G., Löwel, H., Döring, A., Hutchinson, W. L. and Pepys, M. B. (1999) C-reactive protein, a sensitive marker of inflammation, predicts future risk of coronary heart disease in initially healthy middle-aged men: results from the MONICA (Monitoring Trends and Determinants in Cardiovascular Disease) Augsburg Cohort Study, 1984 to 1992. *Circulation,* 99: 237-242.
49. Danesh, J., Whincup, P., Walker, M., Lennon, L., Thomson, A., Appleby, P., Gallimore, J. R. and Pepys, M. B. (2000) Low grade inflammation and coronary heart disease: prospective study and updated meta-analyses. *B.M.J.,* 321: 199-204.
50. Zhang, Y. X., Cliff, W. J., Schoefl, G. I. and Higgins, G. (1999) Coronary C-reactive protein distribution: its relation to development of atherosclerosis. *Atherosclerosis,* 145: 375-379.
51. Bhakdi, S., Torzewski, M., Klouche, M. and Hemmes, M. (1999) Complement and atherogenesis. Binding of CRP to degraded, nonoxidized LDL enhances complement activation. *Arterioscler. Thromb. Vasc. Biol.,* 19: 2348-2354.
52. Cermak, J., Key, N. S., Bach, R. R., Balla, J., Jacob, H. S. and Vercellotti, G. M. (1993) C-reactive protein induces human peripheral blood monocytes to synthesize tissue factor. *Blood,* 82: 513-520.
53. de Beer, F. C., Hind, C. R. K., Fox, K. M., Allan, R., Maseri, A. and Pepys, M. B. (1982) Measurement of serum C-reactive protein concentration in myocardial ischaemia and infarction. *Br. Heart J.,* 47: 239-243.
54. Ueda, S., Ikeda, U., Yamamoto, K., Takahashi, M., Nishinaga, M., Nago, N. and Shimada, K. (1996) C-reactive protein as a predictor of cardiac rupture after acute myocardial infarction. *Am. Heart J.,* 131: 857-860.
55. Pietila, K. O., Harmoinen, A. P., Jokiniitty, J. and Pasternack, A. I. (1996) Serum C-reactive protein concentration in acute myocardial infarction and its relationship to mortality during 24 months of follow-up in patients under thrombolytic treatment. *Eur. Heart J.,* 17: 1345-1349.
56. Morrow, D. A., Rifai, N., Antman, E. M., Weiner, D. L., McCabe, C. H., Cannon, C. P. and Braunwald, E. (1998) C-reactive protein is a potent predictor of mortality independently of and in combination with troponin T in acute coronary syndromes: a TIMI 11A substudy. Thrombolysis in myocardial infarction. *J. Am. Coll. Cardiol.,* 31: 1460-1465.
57. Tommasi, S., Carluccio, E., Bentivoglio, M., Buccolieri, M., Mariotti, M., Politano, M. and Corea, L. (1999) C-reactive protein as a marker for cardiac ischemic events in the year after a first, uncomplicated myocardial infarction. *Am. J. Cardiol.,* 83: 1595-1599.
58. de Winter, R. J., Bholasingh, R., Lijmer, J. G., Koster, R. W., Gorgels, J. P. M. C., Schouten, Y., Hoek, F. J. and Sanders, G. T. (1999) Independent prognostic value of C-reactive protein and troponin I in patients with unstable angina or non-Q-wave myocardial infarction. *Cardiovasc. Res.,* 42: 240-245.
59. Nikfardjam, M., Muillner, M., Schreiber, W., Oschatz, E., Exner, M., Domanovits, H., Laggner, A. N. and Huber, K. (2000) The association between C-reactive protein on admission and mortality in patients with acute myocardial infarction. *J. Intern. Med.,* 247: 341-345.
60. Beranek, J. T. (1997) C-reactive protein and complement in myocardial infarction and postinfarction heart failure. *Eur. Heart J.,* 18: 1834-1835.
61. Beranek, J. T. (1998) C-reactive protein in postinfarction heart rupture. *Am. Heart J.,* 136: 563-564.
62. van Leeuwen, M. A., van Rijswijk, M. H., Sluiter, W. J., van Riel, P. L. C. M., Kuper, I. H., van de Putte, L. B. A., Pepys, M. B. and Limburg, P. C. (1997) Individual relationship between progression of radiological damage and the acute phase response in early rheumatoid arthritis. Towards development of a decision support system. *J. Rheumatol.,* 24: 20-27.
63. Boralessa, H., de Beer, F. C., Manchie, A., Whitwam, J. G. and Pepys, M. B. (1986) C-reactive protein in patients undergoing cardiac surgery. *Anaesthesia,* 41: 11-15.
64. Eda, S., Kaufmann, J., Roos, W. and Pohl, S. (1998) Development of a new microparticle-enhanced turbidometric assay for C-reactive protein with superior features in analytical sensitivity and dynamic range. *J. Clin. Lab. Anal.,* 12: 137-144.
65. Baltz, M. L., Rowe, I. F. and Pepys, M. B. (1985) In vivo studies of the clearance of C-reactive protein. *Clin. Exp. Immunol.,* 59: 243-250.
66. Pepys, M. B. Patent Application No. 0119370.5: Therapeutic protein depletion (University College London, filed 2001).
67. Pepys, M. B., Herbert, J., Hutchinson, W. L., Tennent, G. A., Lachmann, H. J., Gallimore, J. R., Lovat, L. B., Bartfai, T., Alanine, A., Hertel, C., Hoffmann, T., Jakob-Roetne, R., Norcross, R. D., Kemp, J. A., Yamamura, K., Suzuki, M., Taylor, G. W., Murray, S., Thompson, D., Purvis, A., Kolstoe, S., Wood, S. P. and Hawkins, P. N. (2002) Targeted pharmacological depletion of serum amyloid P component for treatment of human amyloidosis. *Nature,* 417: 254-259.
68. Thompson, D., Pepys, M. B. and Wood, S. P. (1999) The physiological structure of human C-reactive protein and its complex with phosphocholine. *Structure,* 7: 169-177.

The invention claimed is:

1. A method for the treatment of tissue damage in a subject having an inflammatory and/or tissue damaging condition caused by C-reactive protein (CRP) comprising atherosclerosis, an inflammatory disease, ischemic or other necrosis, traumatic tissue damage, malignant neoplasia, a bacterial infection, a viral infection, a parasitic infection, or an allergic complication of infection selected from the group consisting of rheumatic fever, glomerulonephritis, and erythema nodosum leprosum, and in need of such treatment, which comprises administering to the subject an effective amount of an agent having the general structure of Ligand-liniker-Ligand wherein each Ligand has the general formula:

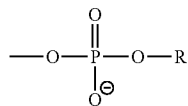

in which R is an amine linked to the —O— by an alkylene group;
wherein the linker has a linear chain structure of —CH$_2$(CH$_2$)CH$_2$— with y having a value from 3 to 18 and the linker enables formation of a complex with CRP in the presence thereof,
wherein
the Ligands are the same or different, and
bind to CRP by ligand binding sites present on CRP.

2. The method according to claim 1 wherein the Ligands are the same.

3. The method according to claim 1, wherein the condition is an inflammatory disease selected from rheumatoid arthritis, juvenile chronic (rheumatoid) arthritis, ankylosing spondylitis, psoriatic arthritis, systemic vasculitis, polymyalgia rheumatica, Reiter's disease, Crohn's disease and familial Mediterranean fever.

4. The method according to claim 1, wherein the condition is tissue necrosis due to anyone of myocardial infarcation, ischaemic stroke, tumour embolization, and acute pancreatitis.

5. The method according to claim 1, wherein the condition is trauma selected from elective surgery, burns, chemical injury, fractures and compression injury.

6. The method according to claim 1, wherein the condition is malignant neoplasia selected from lymphoma, Hodgkin's disease, carcinoma and sarcoma.

* * * * *

UNITED STATES PATENT AND TRADEMARK OFFICE
CERTIFICATE OF CORRECTION

PATENT NO. : 7,615,543 B2  Page 1 of 1
APPLICATION NO. : 10/514127
DATED : November 10, 2009
INVENTOR(S) : Pepys It is certified that error appears in the above-identified patent and that said Letters Patent is hereby corrected as shown below:

In the Claims:

Column 29, lines 16-17, in claim 1 "–$CH_2(CH_2)CH_2$–" should be changed to "–$CH_2(CH_2)_yCH_2$–".

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,615,543 B2
APPLICATION NO. : 10/514127
DATED : November 10, 2009
INVENTOR(S) : Mark B Pepys It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 666 days.

Signed and Sealed this

Nineteenth Day of October, 2010

David J. Kappos
*Director of the United States Patent and Trademark Office*